US006962814B2

(12) United States Patent
Mitchell et al.

(10) Patent No.: US 6,962,814 B2
(45) Date of Patent: Nov. 8, 2005

(54) DECELLULARIZED TISSUE ENGINEERED CONSTRUCTS AND TISSUES

(75) Inventors: Shannon Mitchell, Durham, NC (US); Jennifer Koh, Irvine, CA (US); Vikas Prabhakar, Boston, MA (US); Laura Niklason, Hillsborough, NC (US)

(73) Assignee: Duke University, Durham, NC (US)

( * ) Notice: Subject to any disclaimer, the term of this patent is extended or adjusted under 35 U.S.C. 154(b) by 160 days.

(21) Appl. No.: 09/931,506

(22) Filed: Aug. 16, 2001

(65) Prior Publication Data

US 2002/0115208 A1 Aug. 22, 2002

Related U.S. Application Data

(60) Provisional application No. 60/225,698, filed on Aug. 16, 2000.

(51) Int. Cl.$^7$ .......................... C12N 5/00; A01N 38/00; C12P 21/00; A61K 48/00; A61F 2/02
(52) U.S. Cl. ...................... 435/402; 435/395; 435/70.1; 514/2; 514/44; 623/23.76; 424/93.1; 424/93.2; 424/93.21
(58) Field of Search ...................... 514/2, 44; 435/70.1, 435/402, 395; 424/93.1, 93.2, 93.21; 623/23.76

(56) References Cited

U.S. PATENT DOCUMENTS

| | | | |
|---|---|---|---|
| 4,559,298 A | 12/1985 | Fahy .............................. 435/1 |
| 4,776,853 A | 10/1988 | Klement et al. .............. 8/94.11 |
| 4,890,457 A | 1/1990 | McNally et al. ................ 62/65 |
| D323,895 S | 2/1992 | Protzmann .................. D24/216 |
| 5,131,850 A | 7/1992 | Brockbank ...................... 435/1 |
| 5,145,769 A | 9/1992 | McNally et al. ................ 435/1 |
| 5,158,867 A | 10/1992 | McNally et al. ................ 435/1 |
| 5,192,312 A | 3/1993 | Orton ............................. 623/2 |
| 5,217,860 A | 6/1993 | Fahy et al. ...................... 435/1 |
| 5,266,480 A | 11/1993 | Naughton et al. ..... 435/240.243 |
| 5,336,616 A | 8/1994 | Livesey et al. .......... 435/240.2 |
| 5,364,756 A | 11/1994 | Livesey et al. ................. 435/2 |
| 5,595,571 A | 1/1997 | Jaffee et al. .................. 8/94.11 |
| 5,613,982 A | 3/1997 | Goldstein ..................... 623/11 |
| 5,622,867 A | 4/1997 | Livesey et al. ............... 436/18 |
| 5,632,778 A | * 5/1997 | Goldstein |
| 5,770,417 A | 6/1998 | Vacanti et al. .............. 435/180 |
| 5,780,295 A | 7/1998 | Livesey et al. .......... 435/307.1 |
| 5,855,620 A | * 1/1999 | Bishopric et al. |
| 5,879,383 A | * 3/1999 | Bruchman et al. ............. 623/1 |
| 5,899,936 A | 5/1999 | Goldstein ....................... 623/2 |
| 5,899,937 A | 5/1999 | Goldstein et al. .............. 623/2 |
| 5,916,265 A | 6/1999 | Hu .............................. 623/11 |
| 5,952,168 A | 9/1999 | Wowk et al. ................. 435/1.3 |
| 5,962,214 A | 10/1999 | Fahy et al. ................... 435/1.3 |
| 2002/0160000 A1 | 10/2002 | Niklason et al. ......... 424/145.1 |
| 2003/0235562 A1 | 12/2003 | Niklason et al. ......... 424/93.21 |

FOREIGN PATENT DOCUMENTS

| | | |
|---|---|---|
| EP | 0 528 039 | 2/1993 |
| WO | WO 95/29712 | * 11/1995 |
| WO | WO 97/08295 | 3/1997 |
| WO | WO 97/46266 | * 12/1997 |
| WO | WO 98/46165 | 10/1998 |
| WO | WO 01/49210 | 7/2001 |

OTHER PUBLICATIONS

BD Biosciences, Endothelial Cell Growth Supplement formulation.*

Niklason et al. Functional arteries grown in vitro. Science. Apr. 16, 1999;284(5413):489–93.*

Badar, et al., Tissue Engineering of Heart Valves—Human Endothelial Cell Seeding of Detergent Acellularized Porcine Valves, *Eur. J. Cardio–Thoracic Surg.*, 14:279–284, 1998.

Courtman, et al., "Biomechanical and Ultrastructural Comparison of Cryopreservation and a Novel Cellular Extraction of Porcine Aortic Valve Leaflets", *J. Biomed. Mat. Res.*, 29:1507–1516, 1996.

Gao, et al., "Surface Hydrolysis of Poly(glycolic acid) Meshes Increases the Seeding Density of Vascular Smooth Muscle Cells" *J. Biomed Mater. Res.*, 42: 417–424, 1998.

Niklason, et al., "Advances in Tissue Engineering of Blood Vessels and Other Tissues", *Transplant Immunology*, 5: 303–306, 1997.

Niklason, et al., "Functional Arteries Grown in Vitro", *Science*, 284: 489–493, 1999.

Oberpenning, et al., "De Novo Reconstitution of a Functional Mammalian Urinary Bladder by Tissue Engineering", *Nature Biotechnology*, 17, 149–155, 1999.

Ross, et al., "The Smooth Muscle Cell II. Growth of Smooth Muscle in Culture and Formation of Elastic Fibers" *J. Cell. Biol.* 50: 172–186, 1999.

(Continued)

*Primary Examiner*—David Guzo
*Assistant Examiner*—Daniel M. Sullivan
(74) *Attorney, Agent, or Firm*—Banner & Witcoff, Ltd.

(57) ABSTRACT

New methods for producing tissue engineered constructs and engineered native tissues are disclosed. The methods include producing a tissue engineered construct by growing cells in vitro on a substrate and then decellularizing the construct to produce a decellularized construct consisting largely of extracellular matrix components. The construct can be used immediately or stored until needed. The decellularized construct can be used for further tissue engineering, which may include seeding the construct with cells obtained from the intended recipient of the construct. During any of the growth phases required for production of the construct, the developing construct may be subjected to various tissue engineering steps such as application of mechanical stimuli including pulsatile forces. The methods also include producing an engineered native tissue by harvesting tissue from an animal or human, performing one or more tissue engineering steps on the tissue, and subjecting the tissue to decellularization. The decellularized, engineered native tissue may then be subjected to further tissue engineering steps.

4 Claims, 9 Drawing Sheets

OTHER PUBLICATIONS

Schmidt, et al., "Acellular Vascular Tissues: Natural Biomaterials for Tissue Repair and Tissue Engineering", *Biomaterials*, 21:2215–2231, 2000.

International Search Report issued for corresponding PCT application PCT/US/01/25268.

Allison, S. Dean et al., "Effects of Drying Methods and Additives on Structure and Function of Actin: Mechanisms of Dehydration–Induced Damage and Its Inhibition," *Archives of Biochemistry and Biophysics* (Oct. 1, 1998), pp. 171–181, vol. 358, No.1.

Beattie, Gillian M. et al., "Trehalose: A Cryoprotectant That Enhances Recovery and Preserves Function of Human Pancreatic Islets After Long–Term Storage," *Diabetes*, (Mar. 1997), pp. 519–523, vol. 46.

Elmore, James R. et al., "Cryopreservation affects endothelial and smooth muscle function of canine autogenous saphenous vein grafts," *J. of Vascular Surgery*, (May 1991), pp. 584–592, vol. 13, No. 5.

Ferber, Dan., "Law–Grown Organs Begin To Take Shape," *Science*, (Apr. 16, 1999), pp. 422–425, vol. 284.

Hiles, M.C., et al., "Mechanical properties of xenogenic small–intestinal submucosal when used as an aortic graft in the dog," *J. Biomedical Materials Research*, (1995), pp. 883–891, vol. 29.

Huynh, Tam et al., "Remodeling of an acellular collagen graft into a physiologically responsive neovessel," *Nature Biotechnology*, (Nov. 1999), pp. 1083–1086, vol. 17.

Niklason, L. E., "Replacement Arteries Made to Order," *Science*, (Nov. 19, 1999), pp. 1493–1494, vol. 286.

Rich, S.J. and Armitage, W.J., "Propane–1.2–diol as a Potential Componenet of a Vitrification Solution for Corneas," *Cryobiology*, (1990) pp. 42–54, vol. 27.

* cited by examiner

FIG. 6A
FIG. 6B
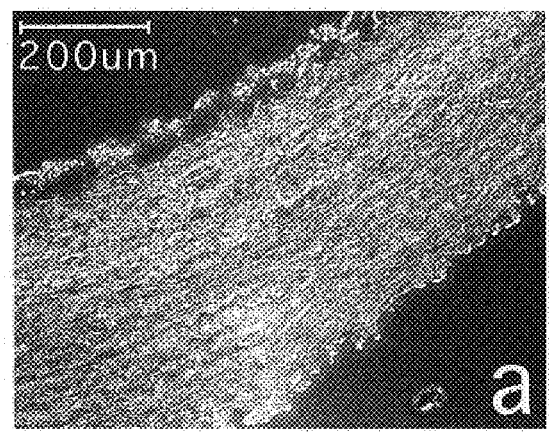

US 6,962,814 B2

DECELLULARIZED TISSUE ENGINEERED CONSTRUCTS AND TISSUES

CROSS-REFERENCE TO RELATED APPLICATION

This application claims priority to U.S. Provisional Patent Application 60/225,698, filed Aug. 16, 2000, the contents of which are hereby incorporated by reference in their entirety.

GOVERNMENT SUPPORT

The U.S. government has a paid-up license in this invention and the right under certain circumstances to require the patent owner to license others on reasonable terms as provided for by the terms of grant number HL-03492 awarded by the NHLBI.

BACKGROUND OF THE INVENTION

Tissue damage, dysfunction, or loss is a feature of a wide variety of medical conditions. Atherosclerosis, in which formation of fatty plaques in blood vessel walls leads to narrowing of the vessels, is one well-known example. Accidents frequently result in damage to tendons, ligaments, and joints. Degenerative diseases such as arthritis represent another source of injury to such tissues. Systemic diseases such as diabetes, cancer, and cirrhosis are yet another cause of organ destruction or dysfunction.

In many of the situations described above, replacement of the damaged tissue or organ is the best or even the only option. Transplantation from human donors (either live or cadaveric) has enjoyed significant success, and procedures such as liver, heart, and kidney transplants are becomingly increasingly common. However, the severe shortage of donors, the complexity of harvesting organs and delivering them to the recipient, and the potential for transmission of infectious agents are significant shortcomings of this approach. In some situations, such as replacement of blood vessels, vessels are removed from one portion of the body and grafted elsewhere to bypass sites of obstruction. However, the number of available vessels is limited, and those available may not be optimal in terms of strength or other parameters.

Use of synthetic materials or tissues derived from animals offer alternatives to the use of human tissues. For example, grafts made of synthetic polymers such as Dacron find use in the replacement of vessels. Mechanical prostheses are widely used to replace damaged heart valves. However, use of synthetic materials has a number of disadvantages. Frequently the material is immunogenic and can serve as a nidus for infection or inflammation. Use of animal tissues also poses problems of immunogenicity as well as the potential to transmit diseases. In addition, harvested animal tissues may be suboptimal in terms of size, shape, or other properties, thus limiting the utility and flexibility of this approach. There is a need for innovative approaches to the problem of replacing damaged or dysfunctional organs and tissues.

Tissue engineering is an evolving field that seeks to develop techniques for culturing replacement tissues and organs in the laboratory (See, for example, Niklason, L. and Langer, R., Advances in tissue engineering of blood vessels and other tissues, *Transplant Immunology,* 5, 303–306, 1997, which is incorporated herein by reference). The general strategy for producing replacement tissues utilizes mammalian cells that are seeded onto an appropriate substrate for cell culture. The cells can be obtained from the intended recipient (e.g., from a biopsy), in which case they are often expanded in culture before being used to seed the substrate. Cells can also be obtained from other sources (e.g., established cell lines). After seeding, cell growth is generally continued in the laboratory and/or in the patient following implantation of the engineered tissue.

Tissue engineered constructs may be used for a variety of purposes including as prosthetic devices for the repair or replacement of damaged organs or tissues. They may also serve as in vivo delivery systems for proteins or other molecules secreted by the cells of the construct or as drug delivery systems in general. Tissue engineered constructs also find use as in vitro models of tissue function or as models for testing the effects of various treatments or pharmaceuticals.

Tissue engineering technology frequently involves selection of an appropriate culture substrate to sustain and promote tissue growth. In general, these substrates should be three-dimensional and should be processable to form scaffolds of a desired shape for the tissue of interest. Several classes of scaffolds are known. These scaffolds fall into five general categories: (1) non-degradable synthetic polymers; (2) degradable synthetic polymers; (3) non-human collagen gels, which are non-porous; (4) non-human collagen meshes, which are processed to a desired porosity; and (5) human (cadaveric) decellularized collagenous tissue. These different scaffold types are further discussed below.

Non-degradable synthetic polymers, e.g., Dacron and Teflon, may be processed into a variety of fibers and weaves. However, these materials are essentially non-biodegradable and thus represent a nidus for infection or inflammation following implantation into the body. Degradable synthetic polymers, including substances such as polyglycolic acid, polylactic acid, polyanhydrides, etc., may also be processed into various fibers and weaves and have been used extensively as tissue culture scaffolds. These materials may be modified chemically to "tune" their degradation rate and surface characteristics. However, fragments of degradable polyesters can trigger significant and undesirable inflammatory reactions.

Non-human collagen gels, e.g., gels made from bovine collagen and rat-tail collagen are convenient materials to work with in the laboratory, but suffer from significant drawbacks including poor tensile strength, no void volume to allow cell growth and tissue development, and sensitivity to collagenases that weaken the gels over time. Non-human collagen meshes consist of porous meshes made from processed bovine collagen. While the utility of these meshes for tissue engineering applications has been little studied, as with all materials made from bovine proteins they carry the risk of immunologic and/or inflammatory reactions when implanted into a human patient as well as the risk of contamination with agents of prion-based disease.

In summary, none of the tissue culture scaffolds presently available is fully satisfactory from all points of view. Thus there exists a need for improved tissue culture scaffolds for use in tissue engineering.

In general, tissue culture scaffolds represent an intermediate in the production of tissue engineered products. The need for improved tissue culture scaffolds represents one aspect of the broader need for improved tissue engineered products for implantation into a human or animal to replace or supplement diseased, damaged, or absent tissues and/or organs. As in the case of animal tissues, tissue engineered tissues created using cells that are not obtained from the intended recipient may be antigenic. On the other hand, when using cells obtained from the intended recipient, a considerable period of time may be required to produce the tissue engineered tissue or organ, given that only a limited number of cells can be harvested. There is therefore a need for improved methods of producing tissue engineered tissues and organs with minimal antigenicity. There is also a need for more flexible methods of producing tissue engineered tissues and organs, for example, methods that would allow use of cells from the intended recipient while minimizing the time required to produce the engineered tissue or organ.

SUMMARY OF THE INVENTION

The present invention provides methods for producing scaffolds for use in tissue engineering and for producing tissue engineered constructs and engineered tissues for implantation into the body. The invention also provides scaffolds for use in tissue engineering, tissue engineered constructs, and engineered tissues suitable for implantation into the body based on the inventive methods. In addition, the invention provides methods for treating an individual in need of replacement or enhancement of a tissue or organ by implantation of the engineered constructs or tissues of the invention.

In one aspect, the invention provides methods for producing decellularized, tissue engineered constructs and also provides decellularized, tissue engineered constructs produced according to the inventive methods. In a preferred embodiment of the method a substrate is seeded (i.e., contacted) with a first population of cells, preferably cells known to secrete extracellular matrix molecules such as collagen and elastin. The substrate can be flat, tubular, or, in general, can be configured to assume any desired three-dimensional shape. In a particularly preferred embodiment of the invention the substrate is tubular. Preferably the substrate consists of a biocompatible material, e.g., a biocompatible polymer having properties or incorporating modifications conducive to cell adherence and/or growth.

Appropriate cell types for seeding the substrate include fibroblasts and smooth muscle cells. In certain embodiments of the invention, the cells used to seed the substrate are derived from an individual of the same species as the individual into which the construct will ultimately be implanted in order to minimize immunogenicity. For example, if the construct is to be implanted into a human being, then human cells may be used to form the primary cell-seeded construct.

The construct is maintained in culture under conditions appropriate for growth of the cells for a growth period during which the cells secrete extracellular matrix molecules. In certain embodiments of the method multiple seedings and growth periods are employed. In certain embodiments of the invention more than one cell type is employed. For example, one or more seedings may be performed with a mixture of cells of different types. Alternatively, each seeding may employ cells of only one type but the same type is not necessarily used for all seedings. In certain embodiments of the invention growth conditions, e.g., tissue culture media, are selected to promote deposition of extracellular matrix. In certain embodiments of the invention stimuli, e.g., pulsatile forces, are applied to the construct during the growth period(s). Such stimuli may be selected to promote the development of desired properties such as mechanical strength.

After the cells have formed a tissue of the desired thickness, the construct is decellularized. Decellularization may be accomplished using any of a variety of detergents, emulsification agents, proteases, and/or high or low ionic strength solutions. In certain embodiments of the invention decellularization is performed under conditions and for sufficient times so that antigenic cells and cellular components are substantially removed, leaving a decellularized tissue engineered construct (scaffold) consisting primarily of extracellular matrix components such as collagen and elastin. In certain embodiments of the invention the substrate that was initially seeded is substantially or entirely removed from the scaffold.

Following the decellularization process, the decellularized construct may be washed to remove components of the decellularization solution. The decellularized construct may be subjected to additional tissue engineering steps as described below. In certain embodiments of the invention the decellularized construct is stored for later use. Different methods may be used to preserve the decellularized construct during storage including cryopreservation and drying according to a variety of protocols. Alternatively, the decellularized construct can be used immediately for further tissue engineering or implanted into the body of a subject. In certain embodiments of the invention the construct is treated with a biologically active agent prior to implantation.

In another aspect, the invention provides methods for producing engineered constructs suitable for implantation into the body. In certain embodiments of the invention, a decellularized tissue engineered construct is prepared from a tissue engineered construct as described above. The decellularized tissue engineered construct is implanted into the body and may recellularize in vivo. In certain embodiments of the invention, prior to implantation, the decellularized construct is treated with any of a variety of agents to enhance the recellularization process.

In an alternative method of the invention, prior to implantation into the body the decellularized tissue engineered construct is seeded with a population of cells to form a seeded decellularized tissue engineered construct. Before this seeding, the construct may be treated in various ways to enhance recellularization. The seeded construct may be implanted into the body of a subject (e.g., an animal, or preferably a human) in need thereof or may be maintained under conditions suitable for the growth and/or differentiation of the cells for a growth period prior to implantation.

In certain embodiments of the invention the cells employed for the seeding are derived from an individual of the same species as the individual into which the engineered construct is to be implanted. The cells may be derived from the same individual into which the engineered construct is to be implanted. A combination of different cell types can be used. For example, the decellularized tissue engineered construct can be seeded with a mixture of cells. Different cell types can be used to seed different portions or surfaces of the construct. In certain embodiments of the invention the cell type(s) are selected in accordance with the ultimate use of the engineered construct. For example, if the construct is to be used as an artery, then appropriate cell types may include vascular cells such as endothelial cells, smooth muscle cells, and fibroblasts. If the construct is to be used to repair a cartilagenous structure, appropriate cell types may include chondrocytes and fibroblasts. In certain embodiments of the invention precursor cells are used to seed the decellularized culture scaffold. The precursor cells may differentiate during the second growth period and/or after implantation into an individual. In certain embodiments of the method multiple seedings and growth periods are employed. In certain embodiments of the invention more than one cell type is employed. For example, one or more seedings may be performed with a mixture of cells of different types. Alternatively, each seeding may employ cells of only one type but the same type is not necessarily used for all seedings. In certain embodiments of the invention stimuli, e.g., pulsatile forces, are applied to the construct during the growth period(s). Such stimuli may be selected to promote the development of desired properties such as mechanical strength.

In another aspect, the invention provides methods for producing decellularized, engineered native tissues and also provides decellularized, engineered native tissues produced according to the inventive methods. The method includes the steps of harvesting native tissue from an animal or human donor, subjecting the native tissue to one or more tissue engineering steps, and decellularizing the engineered native tissue. The tissue engineering step can comprise seeding the native tissue with cells and maintaining the seeded tissue for a growth period under conditions suitable for the growth of the cells. The tissue engineering step can comprise applying a mechanical or electrical stimulus to the native tissue, e.g., a pulsatile stimulus.

Following decellularization the tissue may be implanted into the body of a subject or subjected to further tissue engineering steps. Such steps may include any of the steps mentioned above, e.g., seeding with a population of cells and maintaining the seeded tissue for a growth period under conditions conducive to growth of the cells. The tissue may also be stored and subsequently retrieved for use. In those embodiments of the invention in which the decellularized, engineered native tissue is seeded with cells, the cells may be derived from the individual into whom the tissue is to be implanted. Seeding with cells from the individual into whom the tissue is to be implanted may decrease the likelihood of immune system rejection.

In another aspect, the invention provides methods of treating an individual in need of replacement or enhancement of a tissue or organ. In certain embodiments, the methods comprise producing a decellularized tissue engineered construct or a decellularized engineered native tissue and implanting the construct or tissue into the body of the individual in accordance with standard surgical procedures. In certain embodiments, the methods comprise producing a decellularized tissue engineered construct or a decellularized engineered native tissue, seeding the construct or tissue with cells, and implanting the construct or tissue into the body of the individual in accordance with standard surgical procedures. In certain embodiments of the inventive method the construct or tissue is maintained in culture for a growth period under conditions conducive to growth of the seeded cells prior to implantation into the body of the individual. In certain embodiments of the invention the construct or tissue is seeded with cells that are derived from the individual. After implantation, cells from the individual may migrate into the tissue in vivo, complementing the seeded cell population. The migration of cells into the construct may be enhanced, e.g., by treating the construct with growth factors, chemotactic agents, or other compounds prior to or after implantation. The construct may include cells that are genetically engineered to produce one or more such growth factors, chemotactic agents, etc.

This application refers to various patents, articles, and other publications. The contents of all of these items are hereby incorporated by reference in their entirety.

DEFINITIONS

In order to more clearly and concisely point out the subject matter of the claimed invention, the following definitions are provided for specific terms used in the description and appended claims.

Allogeneic—With respect to a recipient, an allogeneic cell or tissue is a cell or tissue that originates from or is derived from a donor of the same species as the recipient.

Animal—As used herein, the term animal includes humans. Thus when referring to processes such as harvesting tissue from an animal, it is intended that the animal can be a human. Although at times reference will be made herein to "an animal or human", this is not intended to imply that the term "animal" does not include a human.

Artificial substrate—As used herein, the term artificial substrate includes materials such as degradable or non-degradable polymers synthesized in vitro (i.e., not produced by a living animal or plant). Note that the polymer may be identical to a polymer produced by a living plant or animal, e.g., the polymer may be a protein produced using recombinant DNA technology. The substrate can also be, for example, a length of tubing, which may be coated with any of a variety of artificial materials or materials obtained from natural sources. Artificial substrate also encompasses certain materials obtained by isolating and processing substances produced by a living source. In particular, the term encompasses materials obtained by harvesting tissue from an organism and isolating and/or processing one or more extracellular matrix proteins produced by a living source and therefore includes collagen sponges or rafts. However, a tissue that remains substantially intact and substantially retains the structure in which it is naturally found within the body of an organism is not considered an artificial substrate but is instead considered a native tissue. Other than this exception, the term "artificial substrate" is not intended to impose any limitation with respect to either material or configuration.

Autologous—With respect to a recipient, an autologous cell or tissue is a cell or tissue that originates with or is derived from the recipient.

Biologically active agent—A naturally occurring or synthetic chemical entity that is capable of inducing a change in the phenotype or genotype of a cell, tissue, organ, or organism when contacted with the cell, tissue, organ, or organism.

Cellular component—This term refers to substances that constitute a portion of a cell, including cell membranes and macromolecules (e.g., nucleic acids or polypeptides) normally found enclosed within a cell membrane, embedded within a cell membrane, or attached to a cell membrane. The term does not include molecules that have been secreted by cells, e.g., extracellular matrix components such as collagen, elastin, and proteoglycans even if such molecules are linked to the cell surface.

Conditions suitable for growth—Conditions suitable for growth of a particular cell type means an environment with conditions of temperature, pressure, humidity, nutrient and waste exchange, and gas exchange, that are permissive for the survival and reproduction of the cells. With respect to any particular type of cells, an environment suitable for growth may require the presence of particular nutrients or growth factors needed or conducive to the survival and/or reproduction of the cells.

Native tissue—As used herein a native tissue is a tissue that is harvested from an animal or human and that remains substantially intact and substantially retains the structure in which it is naturally found within the body of the animal or human.

Non-cellular structural components—As used herein a non-cellular structural component refers to a substance present within a biological tissue (either a native tissue or a tissue-engineered construct), the substance being derived from a cell that is or was present within the tissue but is not contained within the plasma membrane of a cell. Examples include collagen, elastin, proteoglycans, fibronectin, and laminin.

Precursor cell—The term "precursor cell" refers to a cell that is not fully differentiated but that has the capacity to either become more fully differentiated itself or to give rise to a cell (or cells) that is able to further differentiate. The precursor cell may give rise to one or more different cell types. The process by which the precursor cell gives rise to a cell (or cells) that is able to further differentiate may involve one or more rounds of cell division. A stem cell is one type of progenitor cell. However, the term "progenitor cell" also includes cells that may have undertaken one or more steps along a differentiation pathway, e.g., that express one or more differentiation markers.

Primary cell-seeded construct—A construct comprising an artificial substrate that has been seeded with a population of cells and maintained in culture under conditions suitable for growth and/or division of the cells for a period of time.

Secondary cell-seeded construct—A primary cell-seeded construct that has been seeded with a second population of cells. The second population of cells may be substantially equivalent to the population of cells that was used to produce the primary cell-seeded construct or may differ therefrom.

Tissue engineered construct—This term is generally used herein to refer to a two or three dimensional mass of living mammalian tissue produced primarily by growth in vitro. The construct may include one or more types of tissue, and each tissue may include one or more types of cells. The term also encompasses a two or three dimensional mass of living mammalian tissue produced at least in part by growth in vivo on an artificial substrate. A tissue-engineered construct is distinguished from an explant of a corresponding natural tissue, e.g., a native tissue, in that the primary growth of the construct occurs in vitro.

Xenogeneic—With respect to a recipient, a xenogeneic cell or tissue is a cell or tissue that originates from or is derived from a donor of a different species than the recipient.

BRIEF DESCRIPTION OF THE DRAWING

FIG. 6A shows a phase contrast view of a cross section of a seeded decellularized porcine artery cross section.

FIG. 6B shows a fluorescent cross section of the same sample shown in FIG. 6B.

DETAILED DESCRIPTION OF CERTAIN EMBODIMENTS

Figure 1:
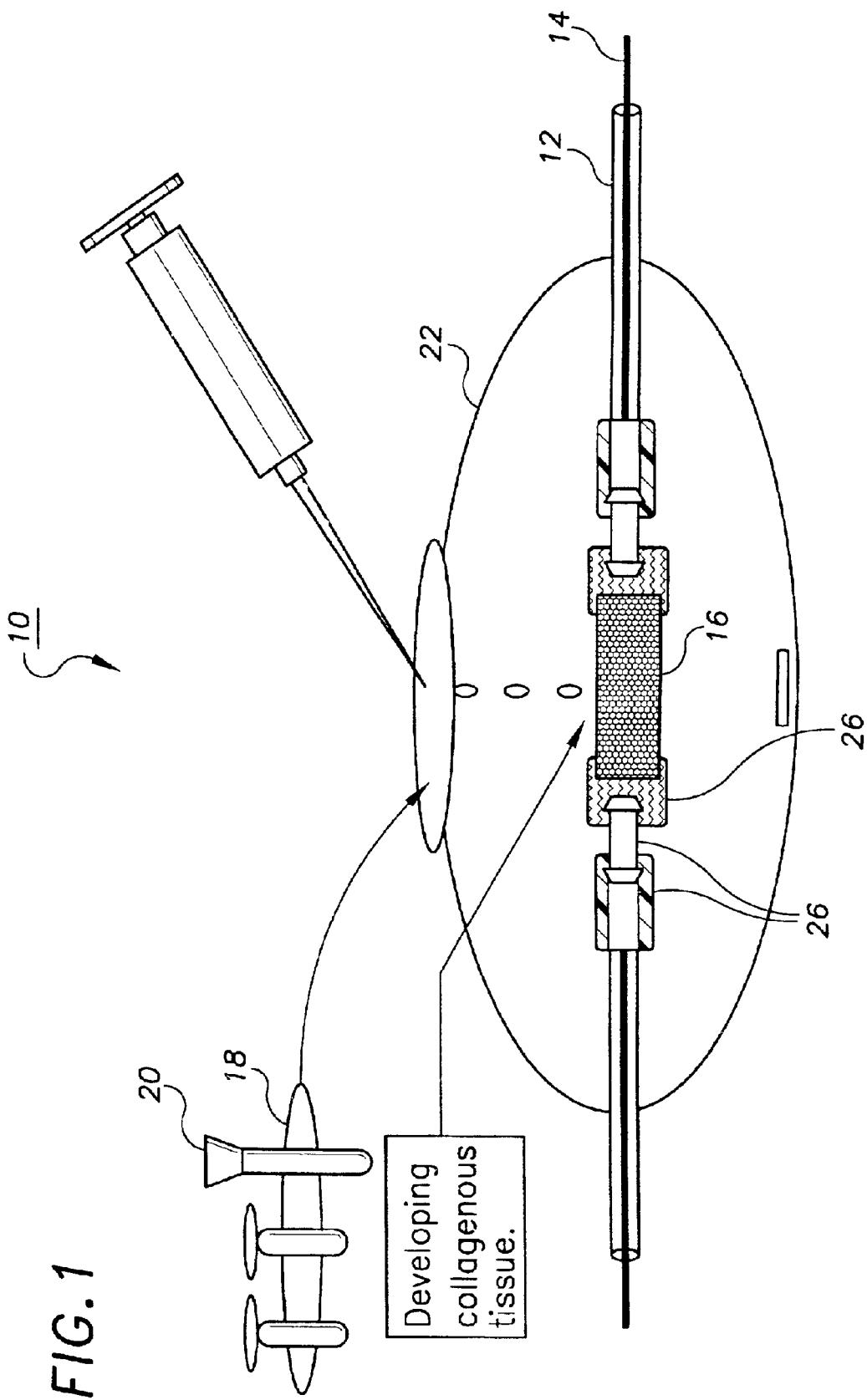
FIG. 1 shows a bioreactor including a tubular substrate suitable for growth of a tissue engineered construct.

The invention provides a variety of new methods and products of utility in the field of tissue engineering and replacement tissues and organs. More specifically, in one aspect the invention provides methods for producing tissue engineered constructs that can be implanted into the body, e.g., as treatments for conditions involving tissue damage or dysfunction. As used herein, implanting into the body includes implanting on the body surface and/or attaching onto the body in addition to implanting within the body so that the implanted construct or tissue is entirely enclosed within the body. Thus the constructs and tissues of the present invention can include replacements for skin, cornea, and other tissues that are not strictly within the body.

In general, the constructs of the present invention are produced by first growing a tissue engineered construct according to any of a variety of methods as described below. Typically these methods involve seeding (i.e., contacting) a substrate with cells and culturing the seeded substrate under conditions suitable for growth of the cells to form a tissue engineered construct. As the cells grow and divide on and/or in the substrate they secrete extracellular matrix proteins such as collagen and elastin. The construct is cultured for a period of time sufficient to produce a construct of desired thickness and/or properties, consisting primarily of secreted proteins and cells. Various growth conditions can be selected to enhance this process and/or to stimulate the development of desirable mechanical, physical, or biochemical properties, etc. Such growth conditions may include the use of particular growth media, the application of mechanical, electrical, and/or chemical stimuli, etc. The cells may be derived from an animal or cell line of the same species as the intended recipient, so that the resulting construct contains proteins that will be minimally antigenic and maximally compatible in the body. For example, if the construct is to be implanted into a human, the cells may be human cells. Although in general production of the tissue engineered construct involves culturing the developing tissue primarily in vitro, tissue engineered constructs produced at least in part by culturing the tissue in vivo are also within the scope of the invention.

In certain embodiments of the invention, production of the tissue engineered construct involves multiple rounds of cell seeding and intervening growth periods. The cells used in different seedings may be of the same or different types and/or may consist of multiple cell types. The growth periods and culture conditions may be the same or may vary between different growth periods. For example, in certain embodiments of the invention, to produce a tissue engineered blood vessel, a substrate is seeded with smooth muscle cells and cultured for a period of time, e.g., 6 weeks. After this first growth period the construct is seeded with endothelial cells and cultured for a further growth period, e.g., 1–2 weeks.

Following production of the tissue engineered construct, regardless of the particular steps employed in its production, the construct is decellularized. Appropriate decellularization techniques remove cellular components while leaving the secreted proteins, e.g., collagen and elastin, substantially intact. Thus, one method of the present invention includes the steps of (i) producing a tissue engineered construct by seeding a substrate with cells, allowing the cells to grow in culture, and optionally subjecting the construct to one or more additional rounds of cell seeding and growth; and (ii) decellularizing the tissue engineered construct, thereby producing a decellularized construct. The first step can include performing various tissue engineering manipulations such as applying mechanical or electrical stimuli to the developing construct, applying selected biologically active agents to the construct (e.g., growth factors). In certain embodiments of the invention the decellularized construct retains substantially the same shape and physical properties as prior to decellularization. In particular, connective tissues such as blood vessels, muscle, bone, tendon, and ligament, all of which have substantial components of extracellular matrix proteins, derive most of their mechanical strength from their extracellular matrix components. The contribution of cells to the physical characteristics of connective tissues is rather small. Thus treatments that remove cells while causing little damage to the extracellular matrix are preferable.

In preferred embodiments of the invention the decellularized construct is thoroughly washed to remove residual decellularization solution that may reduce biocompatibility or inhibit subsequent growth of cells on or in the construct. In certain embodiments of the invention the decellularization process and/or subsequent washing steps result in removal of most or substantially all of the substrate (i.e., the material on which the cells were initially seeded) that remains after the growth period. Following decellularization, the construct can be implanted into the body of a subject or stored before further use. In the latter case, when a patient is in need of an implanted tissue, the construct can readily be reconstituted. Such reconstitution may include the removal of residual storage solution, etc. Thus the inventive method includes one or more of the optional steps of (i) washing the decellularized construct; (ii) removing some or all of the remaining substrate; (iii) storing the decellularized construct; (iv) reconstituting the decellularized construct; and (v) implanting the decellularized construct into a subject.

In contrast to tissues harvested from animal or human donors, the substrate (and therefore the decellularized construct itself) can be configured to assume a particular desired shape and size without the constraints that are imposed by the shape or size of harvested tissue. For example, engineered blood vessels can be grown to a certain desired length or diameter without undesired structures such as side branches or valves. Also, in contrast to decellularized animal tissues, the cell-derived proteins in the decellularized construct can come from cells of the same species as the intended recipient. While not wishing to be bound by any theory, human extracellular matrix proteins are expected to be essentially non-immunogenic when implanted into a human, which may make them preferable to proteins derived from animal sources and also preferable to synthetic degradable or non-degradable polymers. This is so because the extracellular matrix components that make up the non-cellular structural components of a decellularized construct are highly conserved within a species. For example, genetic variants in collagens and elastins are quite rare. Furthermore, cells (e.g., fibroblasts or smooth muscle cells) can be obtained from a single donor and used to produce large numbers (e.g., hundreds) of constructs. These cells may be rigorously screened for transmissible diseases (e.g., HIV or hepatitis), thus decreasing the infectious risk associated with the products. Engineered tissues can be produced using cells that have desirable properties such as an ability to grow well in culture, that have been genetically modified to alter, for example, their secretion of extracellular matrix components, etc.

In certain embodiments of the invention the decellularized construct is used as a scaffold for further tissue engineering. In the case that the scaffold was stored after the decellularization process, the scaffold may be reconstituted as appropriate depending upon the storage technique employed. The decellularized construct, also referred to herein as a scaffold, is seeded with a population of cells, which may be substantially equivalent to the population of cells that was used to seed the substrate or may be different in one or more respects. For example, the cells used to seed the scaffold may be of a different cell type or species from the cells that were used to produce the decellularized construct. In general, the cells are of the same species as the intended recipient and are of a cell type characteristic of the tissue or organ that the construct is intended to replace or augment. For example, if the construct is a blood vessel, the cells preferably include endothelial cells and smooth muscle cells. As in the case of initial production of the tissue engineered construct, multiple rounds of cell seeding and intervening growth periods can be employed. The cells used in different seedings may be of the same or different types and/or may consist of multiple cell types. The growth periods and culture conditions may be the same or may vary between different growth periods. Various growth conditions can be selected to enhance this process and/or to stimulate the development of desirable mechanical, physical, or biochemical properties, to stimulate migration of cells into the wall of the construct, etc. Such growth conditions may include the use of particular growth media, the application of mechanical, electrical, and/or chemical stimuli, etc. Thus, in general, the decellularized construct (scaffold) may be subjected to any of the tissue engineering steps involved in production of a tissue engineered construct.

In certain embodiments of the invention the decellularized construct is seeded with cells obtained from the individual who is the intended recipient of the construct. This approach minimizes the likelihood that the construct will cause an immunological or inflammatory reaction when implanted into the recipient. This embodiment of the invention represents an especially advantageous strategy for the production of a cell-based implantable tissue. For example, using current techniques it takes approximately 6–10 weeks of culture time to produce an implantable tissue engineered artery from cells that are seeded and grown on degradable polymer scaffolds (Niklason, et al., Functional arteries grown in vitro, *Science*, 284: 489–93,1999). The availability of decellularized and mechanically robust collagenous scaffolds as provided by the present invention dramatically shortens this production time. According to one embodiment of the inventive methods, when a patient who would benefit from an implantable vessel is identified, a small biopsy is taken from the patient and the cells isolated. The cells are then seeded onto a decellularized scaffold and grown in culture for a period of several days to one or two weeks. Then the complete, essentially autologous vessel is implanted. This approach reduces the total culture time to produce an autologous vessel from 6–10 weeks to 1–2 weeks, a reduction with profound implications from the point of view of clinical applicability. Of course the methods have similar benefit with respect to other implantable tissues, e.g., heart valves, bladders, etc.

The scaffold may be treated in any of a variety of ways either before or after seeding. For example, agents selected to enhance the adherence or growth of the cells may be applied to the scaffold. After seeding, the seeded scaffold may be implanted into a subject or may be cultured for one or more additional growth periods (i.e., in addition to the period(s) of growth prior to decellularization). In the latter case, various growth conditions can be selected to enhance cell growth and division and/or to stimulate the development of desirable mechanical, physical, or biochemical properties, to stimulate migration of cells into the wall of the scaffold, etc. Such growth conditions may include the use of particular growth media, the application of mechanical, electrical, and/or chemical stimuli, etc.

Thus in summary the inventive methods optionally include the additional steps of (i) seeding the scaffold (i.e., the decellularized construct) with a population of cells, thereby obtaining a cell-seeded decellularized construct; and (ii) implanting the cell-seeded decellularized construct into a subject. Prior to the second of these steps the construct may be maintained in culture for a period of time under conditions suitable for growth and/or division of the cells, thereby producing a tissue engineered decellularized construct. As in the case of production of the initial tissue engineered construct, the tissue engineered, recellularized, decellularized construct may be subjected to multiple rounds of cell seeding and growth, each of which may involve different cell type(s) and/or different growth conditions. During one or more growth periods the tissue engineered decellularized construct may be subjected to various tissue engineering manipulations such as the application of mechanical or electrical stimuli.

In general, the constructs of the present invention can be treated with any of a variety of biologically active agents prior to implantation into a subject. In certain embodiments of the invention these agent(s) are selected to enhance the properties of the construct following implantation, e.g., to facilitate the ability of endogenous cells (i.e., cells present within the subject) to populate the construct, to enhance the growth of seeded cells, to facilitate vascularization of the construct, to reduce the likelihood of thrombus formation, etc. Appropriate biologically agents include, but are not limited to, thrombomodulators, agents that increase hemocompatibility, and antibiotics. In certain embodiments of the invention the biologically active agent comprises a pharmaceutical composition. In this case the construct may serve as a drug delivery vehicle. The pharmaceutical composition may be intended for treatment of the same condition as that being treated by implanting the construct or for treatment of a different condition.

In addition to the decellularization of constructs obtained through tissue engineering techniques (e.g., constructs obtained by seeding an artificial substrate), the present invention also encompasses the decellularization of native tissue that has been subjected to certain tissue engineering step(s) prior to decellularization. For example, the native tissue may be cultured for a period of time under conditions suitable for growth and division of the cells contained therein after harvesting. The native tissue may be seeded with additional cells. The growth conditions (e.g., the growth medium) may be selected to enhance cell growth and division and/or to stimulate the development of desirable mechanical, physical, or biochemical properties. For example, mechanical or electrical forces may be applied to the native tissue. Following the tissue engineering steps the native tissue is decellularized and may then be stored, implanted into the body of a subject, or used as a scaffold for further tissue engineering. In the latter case, the decellularized native tissue is seeded with a population of cells and may then be used or further processed in essentially the same manner as the decellularized constructs described above.

In the following sections, techniques and conditions for production of a primary cell-seeded construct, techniques for decellularization of the primary cell-seeded construct to produce a decellularized construct (scaffold), methods for storage of the scaffold, and methods for reconstitution of the scaffold after storage are described in further detail. Methods for using the scaffold to produce a tissue engineered construct for implanting into the body are also described in more detail below. In addition, tissue engineering steps that may be applied to a harvested native tissue prior to decellularization are described.

In certain embodiments of the invention the construct to be decellularized comprises a tissue engineered construct produced as described in the pending patent application entitled, "Tissue-Engineered Constructs", Ser. No. 09/109,427, filed Jul. 2, 1998.

Production of a Tissue Engineered Construct

Numerous methods and techniques for producing tissue engineered constructs are known in the art and are appropriate for use in conjunction with the present inventive methods. Examples of suitable seeding and culturing methods for the growth of three-dimensional cell cultures are disclosed in pending application "Tissue-Engineered Constructs" Ser. No. 09/109,427; U.S. Pat. No. 5,266,480, and U.S. Pat. No. 5,770,417, all three of which are incorporated herein by reference. These references disclose techniques for establishing a three-dimensional matrix, inoculating the matrix with the desired cells, and maintaining the culture. In general, a tissue engineered construct is produced by seeding cells onto an appropriate substrate and culturing the cells under conditions suitable for growth. The substrate can be flat, tubular, or, in general, can be configured to assume any desired three-dimensional shape. For example, the substrate may be formed into shapes including but not limited to spheres, ellipsoids, disks, sheets, or films as well as hollow spheres, hollow ellipsoids, and open-ended, hollow tubes. In certain embodiments of the invention the substrate is tubular.

In certain embodiments of the invention the substrate comprises a biocompatible material, e.g., a biocompatible polymer having properties or incorporating modifications conducive to cell adherence and/or growth. Suitable materials include materials that are biodegradable or bioerodable, such as materials that hydrolyze slowly under physiological conditions. Porous materials are preferred in certain embodiments of the invention. Among the various suitable materials are synthetic polymeric materials such as polyesters, polyorthoesters, or polyanhydrides, including polymers or copolymers of glycolic acid, lactic acid, or sebacic acid. Substrates comprising proteinaceous polymers are also suitable for production of tissue engineered constructs. Collagen gels, collagen sponges and meshes, and substrates based on elastin, fibronectin, laminin, or other extracellular matrix or fibrillar proteins may be employed. Either synthetic polymers or proteinaceous polymers may be modified or derivatized in any of a variety of ways, e.g., to increase their hydrophilicity and/or provide improved cell adhesion characteristics. In certain embodiments of the invention the substrate is coated with a material, e.g., denatured collagen, prior to seeding in order to increase adherence of the cells thereto. Materials useful as substrates for growing cells to produce tissue engineered substrates, and methods of producing such substrates are known in the art and are described in pending application "Tissue-Engineered Constructs", Ser. No. 09/109,427, and in U.S. Pat. No. 5,770,417.

In certain embodiments of the invention some or all of the substrate degrades during the growth period and/or is removed prior to implantation of the construct into a subject. Removal may be accomplished by application of a fluid flow and may be enhanced by decellularization. In certain embodiments of the invention a tissue engineered construct is grown on a structure from which it is completely removed after a growth period. For example, a vascular construct may be grown on a length of silicone tubing that has been coated with a thin layer of dilute, denatured human collagen to which cells can adhere. After the growth period the silicone tubing is removed from the vascular construct, resulting in a tissue engineered construct entirely free of substrate.

A number of different cell types or combinations thereof may be employed in the present invention, depending upon the intended function of the tissue engineered construct being produced. These cell types include, but are not limited to: smooth muscle cells, cardiac muscle cells, epithelial cells, endothelial cells, urothelial cells, fibroblasts, myoblasts, chondrocytes, chondroblasts, osteoblasts, osteoclasts, keratinocytes, hepatocytes, bile duct cells, pancreatic islet cells, thyroid, parathyroid, adrenal, hypothalamic, pituitary, ovarian, testicular, salivary gland cells, adipocytes, and precursor cells. For example, smooth muscle cells and endothelial cells may be employed for muscular, tubular constructs, e.g., constructs intended as vascular, esophageal, intestinal, rectal, or ureteral constructs; chondrocytes may be employed in cartilaginous constructs; cardiac muscle cells may be employed in heart constructs; hepatocytes and bile duct cells may be employed in liver constructs; epithelial, endothelial, fibroblast, and nerve cells may be employed in constructs intended to function as replacements or enhancements for any of the wide variety of tissue types that contain these cells. In general, any cells may be employed that are found in the natural tissue to which the construct is intended to correspond. However, in some cases it may be advantageous to employ cells of a type that is not naturally found in the tissue to which the construct is intended to correspond. In addition, progenitor cells, such as myoblasts or stem cells, may be employed to produce their corresponding differentiated cell types. In some instances it may be preferred to use neonatal cells or tumor cells.

In certain embodiments of the invention the cells are allogeneic to the intended recipient rather than xenogeneic. Cells may be obtained from a donor (either living or cadaveric) or derived from an established cell line. To obtain cells from a donor (e.g., a potential recipient of a tissue engineered construct), standard biopsy techniques known in the art may be employed. Representative techniques are described, for example, in pending application "Tissue-Engineered Constructs", Ser. No. 09/109,427 and in Oberpenning, F., et al., De novo reconstitution of a functional mammalian urinary bladder by tissue engineering, *Nature Biotechnology*, 17, 149–155, 1999. The contents of this article, which also describes appropriate materials and techniques for creation of three-dimensional substrates, cell culture and cell seeding techniques, and methods for evaluation of tissue engineered organs, are incorporated herein by reference. Cells so obtained may be expanded in culture, although preferably cells of a low passage number (e.g., less than 5 or, more preferably, less than 3) are used to produce the construct in order to minimize loss of the differentiated phenotype. Preferably cells isolated from a donor are screened to eliminate the potential for transmission of infectious diseases. Cells derived from established cell lines (e.g., those available from the ATCC, Rockville, Md.) may also be used. In certain embodiments of the invention cells (either obtained from a donor or from an established cell line) that have been genetically manipulated by the introduction of exogenous genetic sequences or the inactivation or modification of endogenous sequences are employed. For example, genes may be introduced to cause the cells to make proteins that are otherwise lacking in the host. Production of scarce but desirable proteins (in the context of certain tissues) such as elastin may be enhanced.

As mentioned above, in order to minimize antigenicity in certain embodiments of the invention cells from the same species as the intended recipient of the final construct are employed to create the initial tissue engineered construct (i.e., the construct that is to be decellularized). Thus if the construct is to be implanted into a human, preferably cells derived from a human are used to create the initial construct. In those embodiments of the invention in which the decellularized construct is employed as a scaffold for further tissue engineering (i.e., those embodiments in which the decellularized construct is seeded with cells), cells from the same species as the intended recipient of the final construct are preferably used to seed the decellularized construct. In certain embodiments of the invention the decellularized construct is seeded with cells harvested from the intended recipient of the construct. General mammalian cell culture techniques, cell lines, and cell culture systems that may be used in conjunction with the present invention are described in Doyle, A., Griffiths, J. B., Newell, D. G., (eds.) *Cell and Tissue Culture: Laboratory Procedures*, Wiley, 1998, the contents of which are incorporated herein by reference.

In certain embodiments of the invention mammalian cells are seeded onto and/or within a substrate from a suspension so that, preferably, they are evenly distributed at a relatively high surface and/or volume density. The substrate may be, but need not be, a porous substrate. The cell suspensions may comprise approximately $1\times10^4$ to $5\times10^7$ cells/ml of culture medium, more preferably approximately $2\times10^6$ cells/ml to $2\times10^7$ cells/ml, and yet more preferably approximately $5\times10^6$ cells/ml. The optimal concentration and absolute number of cells may vary with cell type, growth rate of the cells, substrate material, and a variety of other parameters. The suspension may be formed in any physiologically acceptable fluid, preferably one that does not damage the cells or impair their ability to adhere to the substrate. Appropriate fluids include standard cell growth media (e.g., DMEM with 10% FBS).

The cells may be seeded onto and/or within a substrate by any standard method. For example, the substrate may be seeded by immersion in a cell suspension for a period of time during which cells adhere to the substrate, followed by washing away the nonadherent cells. The substrate may be seeded with cells using a syringe, pipet, or other sterile delivery apparatus. According to a preferred method the cell suspension is dripped onto the substrate, and the substrate is subsequently rotated, e.g., in a rotating vessel to promote even distribution of the cells.

Following seeding of the cells, in certain embodiments of the invention the cells are allowed to adhere to the substrate for a period of time (seeding time) prior to placing the seeded substrate in tissue culture medium. The optimum seeding time varies with cell type and substrate. For example, when using the synthetic hydrophilic polymeric substrates disclosed in pending application "Tissue-Engineered Constructs", Ser. No. 09/109,427, seeding times of approximately 20 minutes may be used. For other substrates, seeding times of an hour or more may be appropriate and have been employed in the prior art.

Various treatments may be applied to enhance adherence of cells to the substrate and/or to each other. Appropriate treatments are described, for example, in the above-mentioned pending application and in U.S. Pat. No. 5,613,982. Such treatments include the application of various proteins, e.g., growth factors or extracellular matrix proteins to the substrate or to the growing construct. For example, collagen, elastin, fibronectin, laminin, or proteoglycans may be applied to the substrate. The substrate can be impregnated with growth factors such as aFGF, bFGF, PDGF, TGFβ, VEGF, etc., or these agents may be provided in the culture medium.

Appropriate growth conditions for mammalian cells in culture are well known in the art. Cell culture media generally include essential nutrients and, optionally, additional elements such as growth factors, salts, minerals, vitamins, etc., that may be selected according to the cell type(s) being cultured. Particular ingredients may be selected to enhance cell growth, differentiation, secretion of specific proteins, etc. In general, standard growth media include Dulbecco's Modified Eagle Medium, low glucose (DMEM), with 110 mg/L pyruvate and glutamine, supplemented with 10–20% fetal bovine serum (FBS) or calf serum and 100 U/ml penicillin are appropriate as are various other standard media well known to those in the art. A particularly preferred culture medium for producing a muscular, tubular tissue engineered construct such as a small caliber blood vessel is described in Example 2 below. Preferably cells are cultured under sterile conditions in an atmosphere of 5–15% $CO_2$, preferably 10% $CO_2$, at a temperature at or near the body temperature of the animal of origin of the cell. For example, human cells are preferably cultured at approximately 37° C.

In general, the length of the growth period will depend on the particular tissue engineered construct being produced. The growth period can be continued until the construct has attained desired properties, e.g., until the construct has reached a particular thickness, size, strength, composition of proteinaceous components, and/or a particular cell density. Methods for assessing these parameters are described in pending application "Tissue-Engineered Constructs", Ser. No. 09/109,427, and in U.S. Pat. No. 5,613,982.

Following a first growth period the construct can be seeded with a second population of cells, which may comprise cells of the same type as used in the first seeding or cells of a different type. The construct can then be maintained for a second growth period which may be different in length from the first growth period and may employ different growth conditions. Multiple rounds of cell seeding with intervening growth periods may be employed.

In certain embodiments of the invention a muscular, tubular tissue engineered construct is grown in a biomimetic system such as that described in pending application "Tissue-Engineered Constructs", Ser. No. 09/109,427 and in Niklason, et al., Functional arteries grown in vitro, *Science*, 284: 489–93,1999. As described therein, a semi-disposable glass bioreactor similar to that shown in FIG. 1 and discussed in Example 1 of the present application is attached to a pump system. As shown in FIG. 1, the bioreactor chamber 22 includes side arms 12 through which a length of tubing 14 is inserted. The tubing serves as a support for a substrate 16 which is seeded to produce the construct. Alternately, the tubing itself may serve as a substrate either with or without a layer or layers of coating material. Fluid can be pumped through the tubing to impart a pulsatile force to the lumen of the developing construct as discussed below. The bioreactor includes a stopper 18 that can be removed to place the substrate within the reactor and to seed the substrate with cells. Culture medium and other fluids are added to and removed from the chamber via a medium fill port 20. The bioreactor system may be made of glass or of another appropriate material such as various plastics. In those embodiments of the invention in which the decellularized construct is cryopreserved, the bioreactor is preferably made of a material such as plastic capable of withstanding extremely low temperatures (e.g., that of liquid nitrogen).

Application of Stimuli During Growth Period

Tissues within the body are subjected to a variety of physical stimuli. For example, arteries, heart valves, and heart chambers are exposed to pulsatile stretch and flow forces as blood is pumped through the cardiovascular system. Components of the musculoskeletal system are subjected to mechanical forces during walking and other physical activities. It is well established that physical stimuli can exert profound effects on the properties and development of tissues and of the cells that produce these tissues. Without wishing to be bound by any theory, we propose that exposing developing tissue engineered constructs to certain stimuli (e.g., mechanical forces that resemble those to which corresponding tissues would normally be exposed in vivo) will cause the resulting construct to develop properties and structure that more closely resemble those of the corresponding naturally occurring tissue. In some instances the application of appropriate stimuli may result in desirable properties, e.g., increased strength, that exceed those found in the naturally occurring tissue. Therefore, in certain embodiments of the invention a physical stimulus (e.g., a mechanical or electrical stimulus) is applied to the tissue engineered construct during the growth periods. The strength and nature of the stimulus may be varied during the growth period, and the stimulus need not be applied continuously throughout the growth period but may be applied during one or more portions of the growth period. In the case of a construct that is produced by performing multiple rounds of cell seeding with intervening growth periods, different stimuli may be employed during different growth periods.

In certain embodiments of the present invention, as described in detail in pending application "Tissue-Engineered Constructs" Ser. No. 09/109,427, a muscular, tissue engineered construct is produced in which a distensible body is inserted within the lumen of a substrate to provide pulsatile stretch to seeded muscle cells. While the muscle tissue is growing on and/or within the substrate, a pump in communication with the interior of the distensible body provides cyclic increases in pressure to cause the distensible body to distend within the lumen of the substrate and impart a pulsatile stretching force to the substrate and the developing tissue. The application of pulsatile stretching forces may be used in the production of both vascular tissue engineered constructs and muscular, nonvascular constructs such as esophageal, intestinal, rectal, ureteral, or bladder constructs. The forces applied to the construct may be selected to mimic corresponding natural forces in terms of pulsation and the degree of stretch imparted to the construct.

In certain embodiments of the invention forces are applied to a muscular, tubular tissue engineered construct without the use of a distensible tube. For example, fluid such as tissue culture medium can be pumped directly through the lumen of the construct, thus mimicking intraluminal flow as found in arteries in the body. The flow may be varied as the construct develops, and the intraluminal pressure and shear forces may even be increased beyond those found in the body.

Of course the application of physical forces is not limited to muscular and/or tubular tissue engineered constructs but may be advantageously employed in the production of a variety of other types of tissue engineered constructs. For example, pulsatile flow can be employed in the production of heart valves as described in U.S. Pat. No. 5,899,937, the contents of which are herein incorporated by reference. The application of stimuli is not limited to the application of pulsatile stimuli, stretching forces, or stimuli related to fluid flow. For example, compressive stimuli, either constant or cyclical may be employed. In addition, non-mechanical stimuli such as electrical stimuli may be employed.

Decellularization

The methods discussed in this section may be applied to a tissue engineered construct produced according to any of the methods described above or to a native tissue that has been harvested from a subject. In the former case, the result of decellularizing is to produce a decellularized, tissue engineered construct. The decellularized, tissue engineered construct can be implanted into a subject, subjected to further tissue engineering steps that may include seeding with cells, or used for other purposes. A native tissue can be subjected to tissue engineering steps before decellularization to produce an engineered, decellularized native tissue. Of course the engineered, decellularized native tissue can be subjected to additional tissue engineering steps after decellularization.

Decellularization has a number of effects. In particular, in the case of a tissue engineered construct that is produced using cells that are allogeneic to an intended recipient (i.e., cells that are derived from the same species as the recipient), the extracellular matrix proteins such as collagen and elastin that make up a large portion of the construct are substantially non-immunogenic when implanted into the recipient. However, the cells themselves are generally immunogenic when implanted into a subject other than the individual from whom the cells were derived (or a genetically identical individual). For example, pure human collagen (either obtained from human tissue or produced using recombinant DNA technology) is generally non-immunogenic when implanted into a human subject. However, human cells that produce collagen are generally immunogenic when implanted into a human being other than the individual from which they were derived. In other words, in a typical tissue engineered construct the cells constitute the majority of the antigenic material in the construct. Therefore, by removing the cells, it is possible to substantially reduce or eliminate the likelihood that an immunologic or inflammatory reaction will be induced upon implanting the construct into a subject.

Any of a number of decellularization methods can be employed. In general the methods employ a variety of chemical, biochemical, and/or physical means to disrupt, degrade, and/or destroy cellular components and/or modify the matrix in which the cells are embedded so as to facilitate removal of the cells and cellular components. Such methods are disclosed, for example, in U.S. Pat. No. 4,776,853, U.S. Pat. No. 5,192,312, U.S. Pat. No. 5,336,616, U.S. Pat. No. 5,595,571, U.S. Pat. No. 5,613,982, U.S. Pat. No. 5,855,620, U.S. Pat. No. 5,899,936, and 5,916,265. The disclosures of these eight patents are incorporated herein by reference. Additional decellularization methods are disclosed in Bader, A., et al., Tissue engineering of heart valves—human endothelial cell seeding of detergent acellularized porcine valves, *Eur. J. Cardio-thoracic Surg.*, 14, 279–284, 1998 and in Courtman, D. W., et al., Biomechanical and ultrastructural comparison of cryopreservation and a novel cellular extraction of porcine aortic valve leaflets, *J. Biomed. Mat. Res.*, 29, 1507–1516, 1996. The contents of these two articles are incorporated herein by reference. Of course the invention is not limited to these decellularization techniques but also includes modifications of these techniques, as well as other techniques currently available or developed in the future.

The decellularization method preferably does not cause gross alteration in the structure of the tissue engineered construct or native tissue or cause substantial alteration in its biomechanical properties. The effects of decellularization on structure may be evaluated by light microscopy, ultrastructural examination, etc. Biomechanical tests, which are well known in the art, may be used to evaluate the effects of various decellularization protocols on tissue properties. Selection and interpretation of such tests will depend, in general, upon the nature of the construct and the purpose for which it is intended. In addition, the treatment preferably does not result in a cytotoxic environment that significantly inhibits subsequent steps such as reseeding in vitro or population of the construct or tissue by cells of a recipient in vivo.

In certain embodiments of the invention the construct or tissue to be decellularized is incubated in one or more decellularization solutions for a period of time sufficient to remove a substantial fraction of the cells and/or cellular components. In general, the decellularization solutions enhance cell lysis and destruction of cellular components, e.g., they contain agents that disrupt and/or degrade cellular constituents such as cell membranes, proteins, nucleic acids, etc. Aqueous hypotonic or low ionic strength solutions facilitate cell lysis through osmotic effects. Such solutions may comprise deionized water or an aqueous hypotonic buffer (e.g., at a pH of approximately 5.5 to 8, preferably approximately 7 to 7.5). Decellularization may be accomplished using a single decellularization solution, or the construct may be incubated sequentially in two or more solutions. Another approach involves immersing the construct in alternating hypertonic and hypotonic solutions.

Suitable decellularization agents include salts, detergent/emulsification agents and enzymes such as proteases, and/or nucleases. Combinations of different classes of detergents, e.g., a nonionic detergent such as Triton X-100® (tert-octylphenylpolyoxyethylene) and an ionic detergent such as SDS (sodium dodecyl sulfate) may be employed. In a particularly preferred embodiment of the inventive method, one or more decellularization solutions that include Triton X-100®, CHAPS (3-[(3-cholamidopropyl)-dimethyl-ammonio]-1-propanesulfonate), or SDS in phosphate buffered saline (PBS) is employed as described in the Examples below. Other suitable detergents include polyoxyethylene (20) sorbitan mono-oleate and polyoxyethylene (80) sorbitan mono-oleate (Tween 20 and 80), sodium deoxycholate, and octyl-glucoside.

In general, it is preferable to employ a decellularization technique that minimizes damage to or alteration of the proteinaceous matrix. Such damage may result from proteases (e.g., collagenase) that may be released upon lysis of cells or that may be present in the matrix extracellularly. Therefore, in certain embodiments of the invention various additives such as metal ion chelators, e.g., EDTA (ethylenediaminetetraacetic acid) and/or protease inhibitors are included in the decellularization solution. Suitable protease inhibitors for use in decellularization solutions include, for example, one or more of the following: phenylmethylsulfonyl-fluoride (PMSF), aprotinin, leupeptin, and N-ethylmaleimide (NEM).

Various enzymes that degrade cellular components may be employed in the decellularization solution. Such enzymes include nucleases (e.g., DNAses such as DNAse I, RNAses such as RNAse A), and phospholipases (e.g., phospholipase A or C). Certain proteases such as dispase II, trypsin, and thermolysin may be of use in decellularization, particularly in decellularization of native tissues such as skin. When employing proteolytic enzymes it may be desirable to take care that removal of cells occurs without significant damage to the extracellular matrix. The activity of proteases is a function of time, temperature, and concentration, and these variables may be appropriately adjusted to achieve acceptable decellularization without unacceptable destruction of the extracellular matrix. Nucleases are typically employed at a concentration of between 0.1 μg/ml and 50 μg/ml, preferably approximately 10 μg/ml for DNAse I and approximately 1.0 μg/ml for RNAse A. The nucleases are preferably employed in a physiologically buffered solution at a temperature of between approximately 20° C. to 38° C., preferably 37° C., for a time between approximately 30 minutes to 6 hours.

As mentioned above, the decellularization solution typically includes a buffer. Suitable buffers include organic buffers such as Tris (hydroxymethyl)aminomethane (TRIS), (N-[2-hydroxyethyl]piperazine-N'-[2-ethanesulfonic acid] (HEPES), etc. Buffers including sodium phosphate, citrate, bicarbonate, acetate, or glutamate may also be used. In general, a pH between about 5.5 and 8.0, between about 6.0 and 7.8, or between about 7.0 and 7.5 is employed.

Physical forces such as the formation of intracellular ice may be employed as a primary means of accomplishing decellularization or to augment the activity of decellularization solutions. One such approach referred to as vapor phase freezing involves placing the construct or tissue in an appropriate solution, e.g., a standard cryopreservation solution such as Dulbecco□s Modified Eagle Medium (DMEM), 10% dimethylsulfoxide (DMSO), 10% fetal bovine serum (FBS) and cooling at a slow rate, e.g., 1–2° C./min. Multiple freeze-thaw cycles may be employed. Colloid-forming materials may be added to the solution to reduce extracellular ice formation while allowing formation of intracellular ice. Appropriate materials include polyvinylpyrrolidone (10% w/v) and dialyzed hydroxyethyl starch (10% w/v).

The examples of decellularization techniques provided above are not intended to be limiting, and the invention encompasses the use of essentially any decellularization technique that removes a substantial fraction of the cells while leaving the matrix substantially intact. Of course it is to be understood that certain techniques will be preferred for particular tissue engineered constructs or native tissues, depending upon the properties of these constructs or tissues. One of ordinary skill in the art will be able to select an appropriate decellularization technique and to vary parameters such as temperature and time in order to achieve a desired degree of decellularization. In certain embodiments of the invention the decellularization process removes at least 50% of the cells. In certain embodiments of the invention the decellularization process removes at least 60%, at least 70%, or at least 80% of the cells. In certain embodiments of the invention at least 90%, at least 95%, or substantially all of the cells are removed. As described above, there may be a tradeoff between the two goals of achieving a high degree of decellularization and preserving the structure and properties of the extracellular matrix. Thus it is not necessarily preferred to achieve maximal possible decellularization if doing so results in unacceptable damage to the extracellular matrix. The optimum degree of decellularization may depend upon the properties of the construct and the use for which it is intended.

Regardless of the decellularization method employed, in certain embodiments of the inventive methods the decellularized construct or tissue is washed in a physiologically appropriate solution such as PBS, tissue culture medium, etc., following removal from the solution in which decellularization was performed. Washing removes residual decellularization solution that might otherwise cause deterioration of the decellularized construct or tissue, inhibit the growth of subsequently seeded cells, and/or reduce biocompatibility.

In certain embodiments of the invention decellularization is performed by soaking the construct in decellularization solution(s) for a period of time. The solution may be stirred or agitated during this period. In addition, it may be desirable to alter the pattern of flow of the decellularization solution, e.g., by establishing convective currents within the container in which decellularization is performed, by employing rotating arms with paddles in appropriate locations in the container, etc. Modifying the flow pattern may improve transport of important decellularization agents in the solution and increase their transfer, improving percent decellurization. In addition, modifying the flow may enhance removal of cells and cellular components from the tissue.

In certain embodiments of the invention in which the construct is an engineered vessel grown in a bioreactor, the decellularization solution can be pumped through the inner lumen of the vessel to decellularize the inner portion of the vessel. In addition, the tissue culture medium can be removed from the bioreactor and replaced with decellularization solution to expose the outer portion of the vessel to decellularizing conditions. Application of pulsatile forces (described above) during the decellularization period may be employed to enhance decellularization.

Following decellularization and washing, the decellularized tissue engineered construct or decellularized engineered native tissue may be implanted into a subject in need thereof, e.g., as a replacement blood vessel, heart valve, organ, etc., or may be subjected to additional tissue engineering steps including seeding with cells. Alternatively, the decellularized construct can be stored for future use as described below.

Evaluating Effects of Decellularization

Figure 2A:
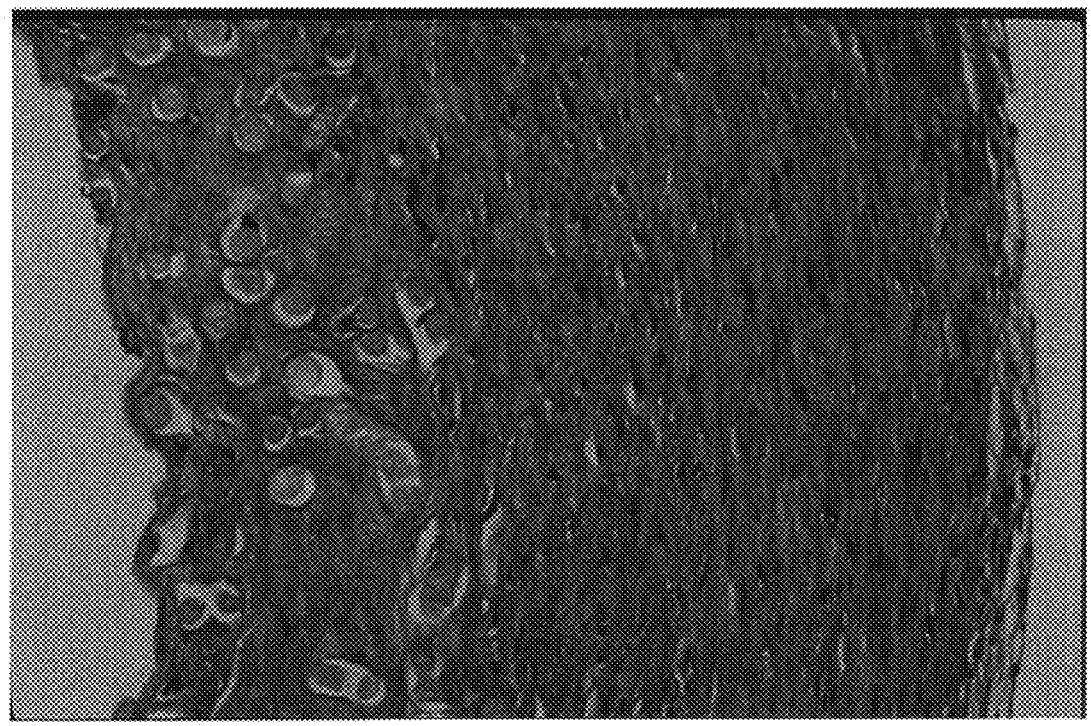
FIG. 2A shows a photomicrograph of an untreated tissue engineered small caliber artery stained with hematoxylin and eosin at 66× magnification.
Figure 2B:
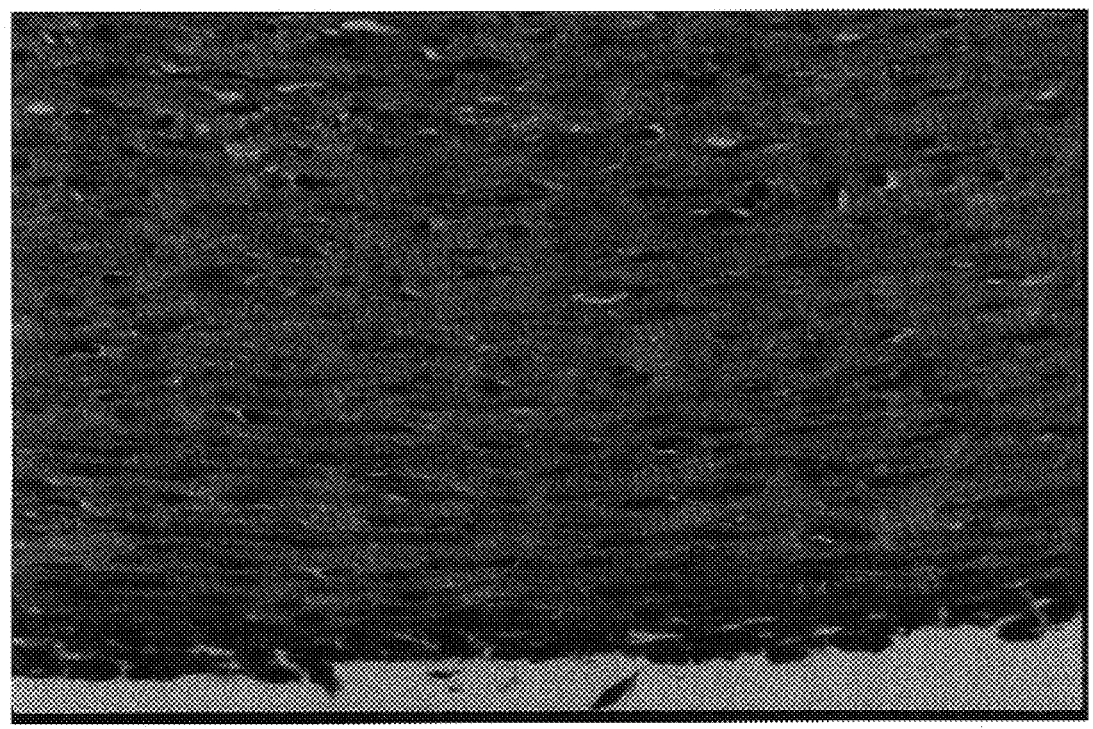
FIG. 2B shows a photomicrograph of an untreated tissue engineered small caliber artery stained with hematoxylin and eosin at 100× magnification.
Figure 3A:
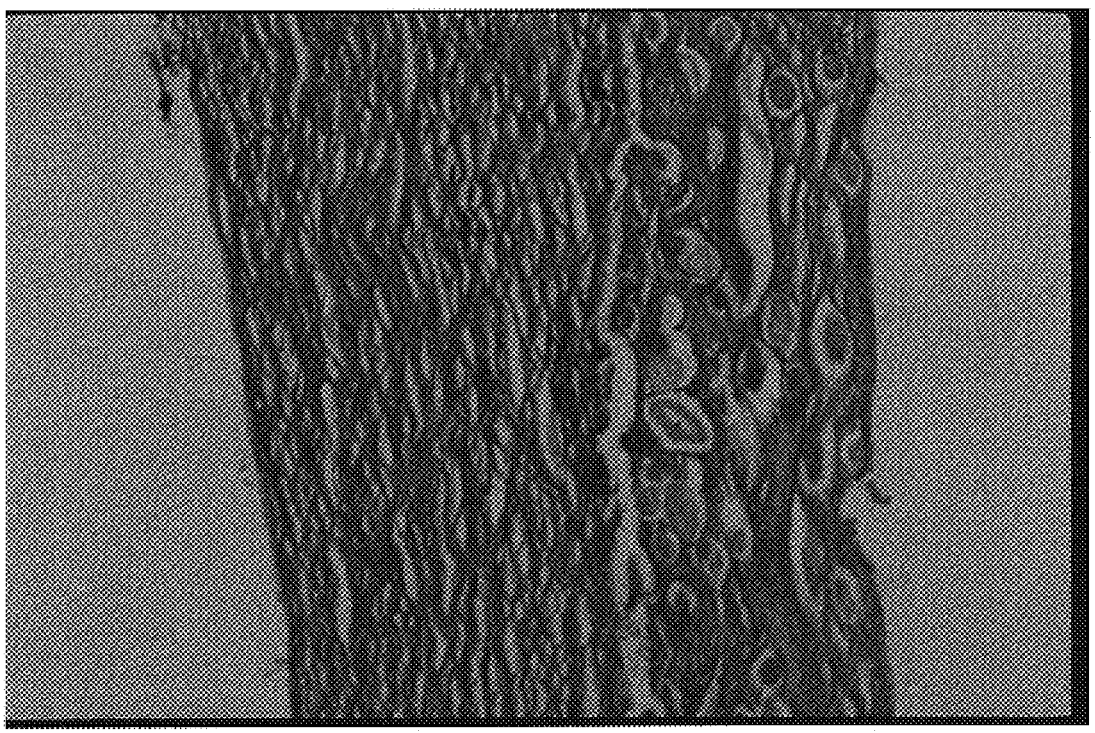
FIG. 3A shows a photomicrograph of a decellularized tissue engineered small caliber artery stained with hematoxylin and eosin at 66× magnification.
Figure 3B:
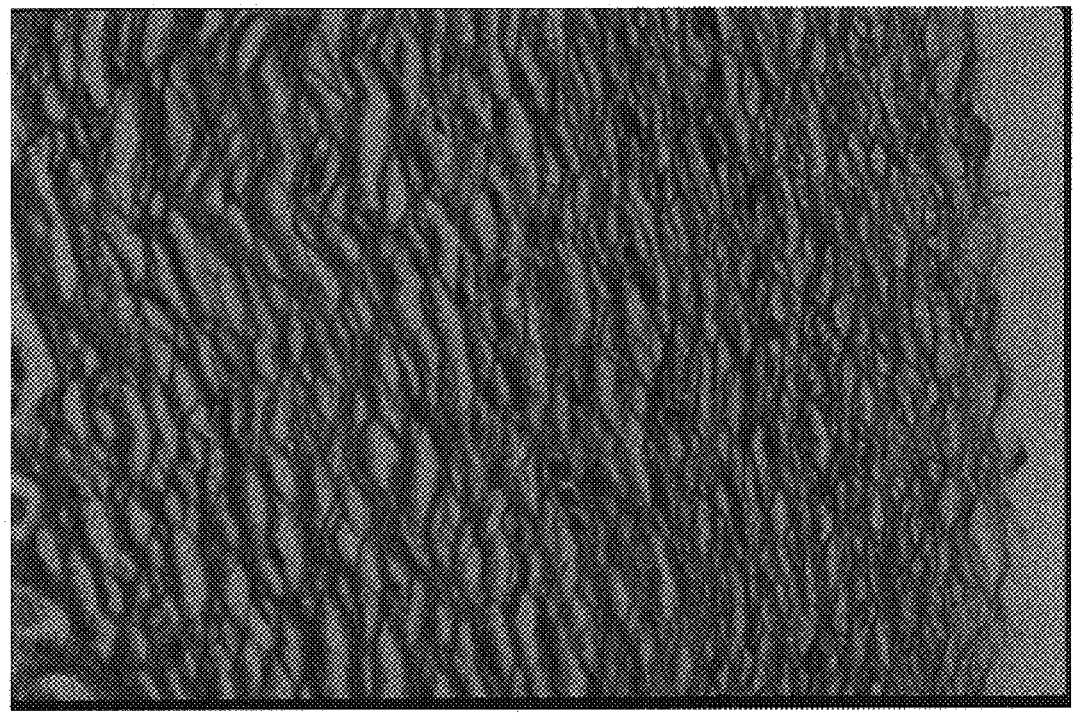
FIG. 3B shows a photomicrograph of a decellularized tissue engineered small caliber artery stained with hematoxylin and eosin at 100× magnification.
Figure 4A:
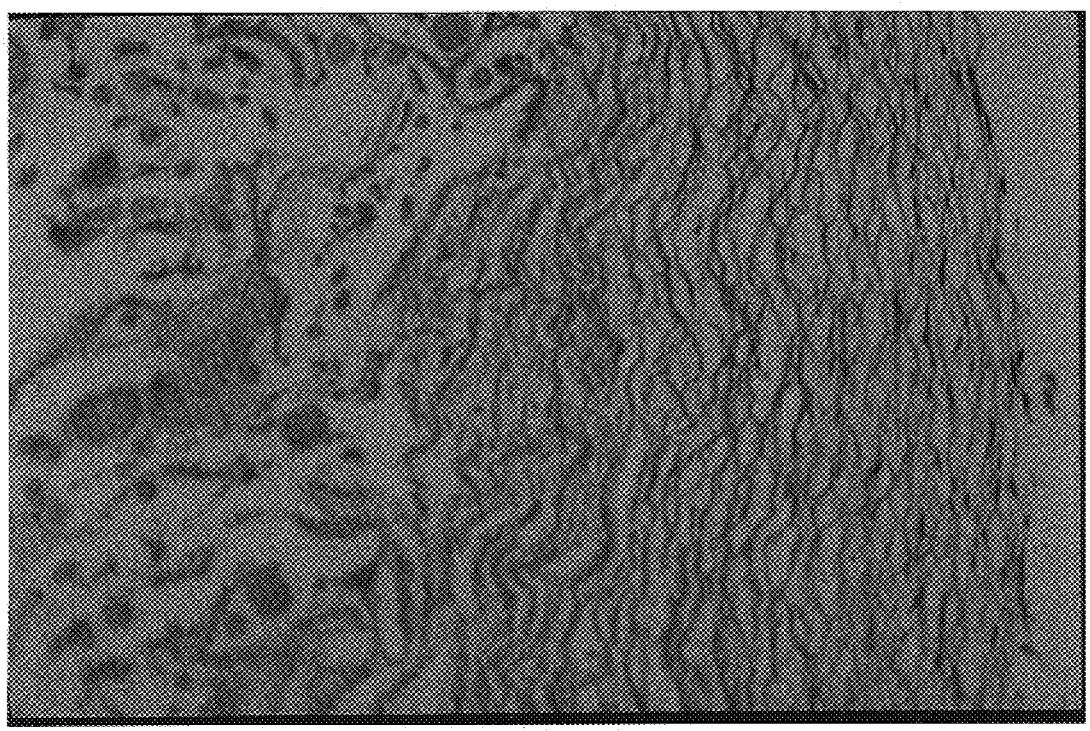
FIG. 4A shows a photomicrograph of a decellularized tissue engineered small caliber bovine artery stained with hematoxylin and eosin at 66× magnification.
Figure 4B:
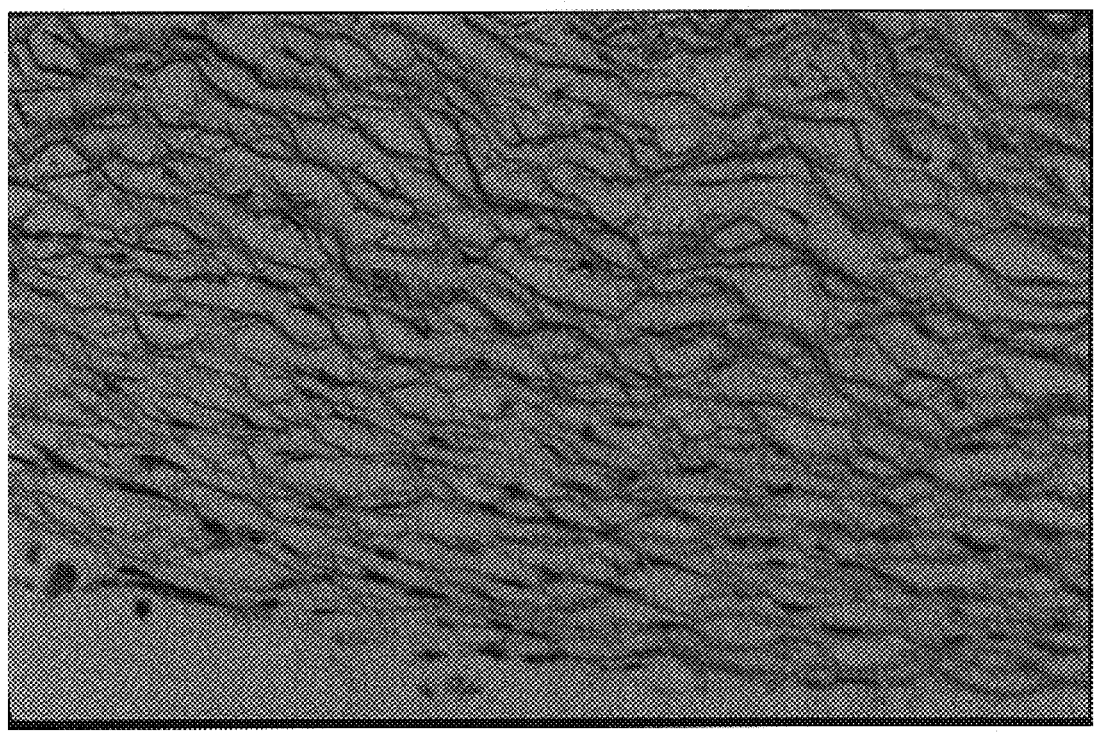
FIG. 4B shows a photomicrograph of a decellularized tissue engineered small caliber bovine artery stained with hematoxylin and eosin at 100× magnification.

Various methods may be used to assess the effects of a particular decellularization protocol in regards to the extent of decellularization achieved and/or in regards to the alterations in the non-cellular structural components (e.g., the extracellular matrix). Samples of the tissue may be stained, e.g., with hematoxylin and eosin, and examined by light microscopy. When hematoxylin and eosin staining is employed extracellular matrix components appear pink, and nuclei appear as purple spots as shown in FIGS. 2, 3, and 4. Staining procedures and stains that differentiate between cells and extracellular matrix, and stains that differentiate between various extracellular matrix components (e.g. collagen and elastin) are well known in the art. The number of cells present in the tissue can be determined by visual inspection at about 20× to 100× magnification. To assess the percent decellularization achieved, the number of cells present in a given area of decellularized tissue is compared with the number of cells present in an equivalent area of control tissue that has not been subjected to decellularization. The integrity of the non-cellular structural components can also be assessed by visual inspection. For example, deterioration in these components may be evidenced by fragmentation or separation between fibrils of extracellular matrix material.

Other techniques for assessing the extent of decellularization include immunohistochemistry and electron microscopy. Immunohistochemistry may be used to detect specific cellular components including components that may be particularly immunogenic such as histocompatibility antigens. Details regarding processing of tissues for light and electron microscopy and for immunohistochemistry may be found in the references cited at the beginning of this section, in particular Bader, et al. Other appropriate techniques are known to those of ordinary skill in the art. An estimate of the density of cells remaining after decellularization may also be obtained by determining the DNA content of the tissue, e.g., by measuring the fluorescence intensity of a dye such as Hoechst 33258 upon binding to DNA as described in pending application "Tissue-Engineered Constructs", Ser. No. 09/109,427.

In certain embodiments of the invention the removal of cells and cellular components results in reduced immunogenicity of the decellularized construct as compared with the construct before decellularization. A variety of approaches may be used to demonstrate the reduced immunogenicity of the decellularized construct. For example, the humoral immune response to extracts made from decellularized constructs may be compared with the humoral immune response to extracts made from control constructs that have not been decellularized (See Example 4 in U.S. Pat. No. 5,613,982). Briefly, rabbits are immunized with NaCl extracts of either decellularized or control constructs, and immune sera are obtained. The immune sera are screened for the presence of IgG and IgM antibodies against antigens present in extracts made from non-decellularized (control) constructs. Another approach to assessing the reduction in immune and inflammatory responses to decellularized constructs compared with control constructs involves implanting samples of the constructs into rabbits, removing the implants and surrounding tissue after a period of time such as two weeks, and subjecting the removed implants and tissue to histopathologic analysis (See Example 5 in U.S. Pat. No. 5,613,982). The presence of inflammatory and immune system cells in the samples serves as an indicator of the degree of the inflammatory and immunologic response triggered by the implants. A variety of other methods known to those skilled in the art may be employed to assess the reduction in immunogenicity and inflammatory response due to decellularization of the tissue engineered constructs.

Storage of a Decellularized Construct

A decellularized construct or decellularized native tissue may be stored after decellularization using any of a number of storage techniques. Storage of decellularized constructs or tissues would provide ready access to these materials when needed. In a particularly advantageous embodiment of the invention, many tissue engineered constructs are prepared using human cells obtained from a single preferred source (e.g., a single human donor whose cells have been screened to reduce the likelihood of transmission of infectious diseases or a cell line that exhibits particularly preferred properties or has been genetically modified to enhance its ability to secrete extracellular matrix components). The tissue engineered constructs are decellularized and stored. When a subject who would benefit from implantation of a tissue engineered construct is identified, a stored construct is reconstituted and either implanted directly into the patient or subjected to further tissue engineering, e.g., seeding with cells obtained from the patient.

Cryopreservation (i.e., preserving by maintaining at an extremely low temperature) is a method for storing the decellularized construct or decellularized native tissue. Freezing and vitrification are two different approaches currently being pursued. In both cases, prevention of destructive ice crystal formation is a major goal. For freezing, the tissue or organ to be cryopreserved is perfused with a solution containing a sufficient concentration (generally approximately 10% by volume) of a cryoprotective agent (CPA) so that ice formation is limited during subsequent cooling. Typical cryoprotectants include glycerol, dimethylsulfoxide (DMSO), glycols, propanediol, polyvinylpyrrolidone, dextran, and hydroxyethyl starch. Vitrification is a cryopreservation technique involving solidification in an amorphous glassy state that minimizes or eliminates ice crystal formation and growth. In both cases, tissues must be typically cooled to temperatures below $-100°$ C. (e.g., in liquid nitrogen) for long-term stability. For vitrification, the tissue is perfused with even higher concentrations of CPA than for freezing. Following incubation in the cryopreservation solution, the tissue may be packaged in a sterile container. In a preferred embodiment of the invention in which a tissue engineered construct is grown and decellularized in a bioreactor, the cryopreservation solution is introduced into the bioreactor, which is used as the storage container.

The choice and concentration of cryoprotectant, timecourse for the addition of cryoprotectant, temperature at which the cryoprotectant is introduced, and rate of cooling and subsequent rewarming all play an important role in the success of preservation procedures. A variety of specific procedures and methods for preservation and reconstitution after storage have been developed and applied to various tissues and cells. Techniques for preserving tissues and organs, including blood vessels, heart valves, muskuloskeletal tissues, and collagenous tissues, by cryopreservation are described, for example, in U.S. Pat. Nos. 4,890,4575; 5,131,850; 5,145,769; 5,158,867 and in U.S. Pat. No. 5,336,616, which discloses a method for preserving an acellular, collagen-based tissue matrix. The method includes incubating a decellularized tissue comprising a proteinaceous matrix with a cryoprotectant solution, followed by freezing at cooling rates such that minimal functional damage occurs to the proteinaceous matrix, drying the cryoprepared tissue under temperature and pressure conditions that permit removal of water without substantial ice recrystallization or ultrastructural damage, storage of the tissue, and subsequent rehydration.

Techniques and reagents for vitrification are described in U.S. Pat. No. 4,559,298; U.S. Pat. No. 5,217,860, U.S. Pat. No. 5,952,168, and U.S. Pat. No. 5,962,214. The contents of the afore-mentioned nine patents are herein incorporated by reference. The methods disclosed in these references will be readily adaptable to the decellularized, tissue engineered constructs and decellularized, engineered native tissues disclosed herein.

Although cryopreservation represents a reliable approach to storing a decellularized tissue engineered construct of the present invention, alternative methods are also within the scope of the invention. For example, drying methods can also be used, with the addition of stabilizing compounds such as sucrose. A dextran and sucrose combination provides desirable physical properties and protein protection against freeze drying and air drying stresses. Freeze drying may take place using a lyophilizer. Air drying may take place under a stream of dry nitrogen, and the construct may then be lyophilized under a vacuum at room temperature.

Reconstitution of a Decellularized Construct

Depending upon the particular storage technique selected, the construct is appropriately reconstituted before being implanted into a subject or used for further tissue engineering. Reconstitution preferably removes cryopreservation agents that are potentially toxic to cells and irritating if introduced into the body. In addition, preferred reconstitution techniques cause minimal alteration in the structural components of the construct. In the case of cryopreservation, reconstitution includes warming (preferably rapidly) and removal of the cryopreservation solution as described in the patents listed above. Removal of the cryopreservation solution may be accomplished by thorough washing, e.g., in normal saline or standard cell culture medium. If drying is employed, reconstitution includes rehydration (e.g., in normal saline or standard cell culture medium), as described in U.S. Pat. No. 5,336,616. Antibiotics and/or antifungal agents may be included in the solutions used for rinsing and/or rehydration to minimize the chance of contamination. Dried tissue can be exposed directly to a cell suspension, thereby reconstituting and seeding in one step. The dried tissue can be rinsed, e.g., with media to remove any drying agents and then soaked in media if needed before exposing the tissue to a cell suspension.

Uses and Further Engineering of a Decellularized Tissue Engineered Construct

As mentioned above, a decellularized tissue engineered construct can be implanted into the body of a subject in order to repair, replace, or augment a tissue or organ in need thereof. Implantation can be performed using any of a variety of techniques, e.g., surgical techniques, known to those of skill in the art and dependent upon the particular function that the construct is intended to fulfill. For example, a decellularized vascular construct may be used in a bypass operation to replace a diseased blood vessel. A decellularized heart valve construct may be used in a valve replacement operation, e.g., to replace a stenotic or incompetent valve. In the case that the decellularized construct is implanted directly into a recipient, the construct may be repopulated in vivo with the recipient's own cells. Various agents such as growth factors, etc., may be applied to the construct to enhance this process. Such agents may be applied, for example, prior to implantation, or after implantation, e.g., by injection into or near the construct, by systemic delivery to the recipient of the construct, etc.

In certain embodiments of the invention the decellularized construct is subjected to further tissue engineering steps prior to implantation into a recipient. Such steps can comprise seeding the construct with one or more populations of cells, preferably cells obtained from the intended recipient. For example, a decellularized vascular construct can be seeded with smooth muscle and/or endothelial cells obtained from a biopsy specimen taken from the intended recipient. After a period of time during which the cells are allowed to adhere to the construct the seeded construct can be implanted into the recipient. In certain embodiments of the invention the cells are genetically transformed so that they exhibit desirable characteristics, e.g., production of a protein or other molecule that is lacking in the recipient or production of a growth factor that stimulates cellularization or angiogenesis in the construct. In other embodiments of the invention the construct is impregnated with a bioactive agent such as a pharmaceutical composition prior to implantation into the recipient and thereby serves as a drug delivery vehicle.

In certain embodiments of the invention the decellularized construct is seeded and cultured for a period of time prior to implantation into the recipient. This growth period may be relatively short (e.g., 1–2 weeks) compared with the time required to grow the construct prior to decellularization. This period allows the seeded cells to become established and commence division. However, since the construct already possesses substantial mass and strength, it is not necessary to culture the cells for long enough to generate an extensive extracellular matrix. Of course the decellularized construct can be subjected to multiple seedings and growth periods. In general, any or all of the techniques employed in the growth of the construct prior to decellularization may be employed during any growth phases that follow decellularization. For example, substances described above may be applied to the decellularized construct to promote adherence of cells. Growth factors may be applied to the construct and/or included in the medium to promote the growth of cells and/or the development or maintenance of a differentiated phenotype. In certain embodiments of the invention stimuli such as those described above (e.g., pulsatile forces and/or fluid flow) are applied to the seeded, decellularized construct during the growth period(s) that follow decellularization.

Thus certain embodiments of the present invention involve producing a tissue engineered blood vessel using a bioreactor system in which pulsatile and fluid flow stimuli are applied to a substrate that is seeded with smooth muscle cells and endothelial cells that are allogeneic to an intended recipient. The substrate is cultured with the application of pulsatile stretch for approximately 6–8 weeks, during which a substantial proteinaceous extracellular matrix is secreted, and the construct attains desired physical properties and thickness. The construct is then decellularized in the bioreactor chamber, with the application of pulsatile forces and fluid flow during the decellularization period to enhance the decellularization process and contribute to removal of the substrate. The decellularized construct is stored until needed. Following identification of an individual in need of a vascular graft, the construct is retrieved from storage and is seeded with smooth muscle and endothelial cells obtained from the intended recipient. After a relatively short culture period (e.g., 1–2 weeks), during which pulsatile stimuli and/or fluid flow may be applied to the construct, the recellularized construct is implanted into the recipient using an appropriate surgical procedure.

Assessing Biomechanical Properties and Cell Viability of Constructs or Tissues

It may be desirable to employ a decellularized construct that displays biomechanical properties similar to or superior to those of the tissue or organ to which they correspond, particularly when the decellularized construct is to be implanted into the body without being subjected to additional tissue engineering steps. A variety of methods may be employed to test the biomechanical properties of decellularized tissue engineered constructs or of decellularized constructs that have been subsequently cell seeded and cultured. The particular technique selected will, in general, depend upon the construct, and the desired biomechanical properties will depend upon the intended function of the construct following implantation into a recipient. Suitable methods for testing the biomechanical properties of a vascular construct are described in pending application "Tissue-Engineered Constructs", Ser. No. 09/109,427 (see Examples therein) and include measurement of burst strengths and compliances and measurement of suture retention strength. Stress-strain analyses such as the single load versus elongation test, the stress relaxation test, and the tensile failure test are described in U.S. Pat. No. 5,613,982 (see Example 7) are also appropriate and may be applied, in general, to any type of tissue engineered construct. Additional tests known to those of skill in the art may also be used.

In those embodiments of the invention in which the decellularized construct is seeded and cultured prior to implantation into a recipient, it my be desirable that the construct is functional and viable prior to implantation. Various methods may be used to assess the functioning and viability of the construct. For example, cell viability may be assessed by trypan blue exclusion assay, by measuring total protein synthesis (e.g., by measuring incorporation of [$^3$H] proline) or DNA synthesis (e.g., by measuring incorporation of [$^3$H] thymidine). More specific assays of cellular activity such as measurement of collagen production are also well known in the art as described in U.S. Pat. No. 5,613,982.

Production of a Decellularized, Engineered Native Tissue

The inventive methods described above involve the decellularization of a tissue engineered construct. However, the methods may be extended to include the decellularization of a native tissue that has been harvested from a donor and subjected to tissue engineering steps prior to decellularization. Methods for harvesting tissues from donors (e.g., living or cadaveric animal or human donors) are well known in the art. Various methods have been employed to harvest vascular tissues, heart valves, skin, organs such as kidneys, livers, lungs, hearts, etc. In some cases tissues or organs are harvested for purposes of transplanting them directly into a recipient, in which case the goal is generally to preserve the tissue or organ in a state as closely approximating the state in which it was removed from the donor as possible, and the harvested tissue or organ is subjected to minimal processing. In other instances, e.g., the harvesting of porcine heart valves to be used as replacements for human heart valves, the harvested tissue may be subjected to extensive chemical processing such as fixation, decellularization, cross-linking, etc., to reduce immunogenicity and/or to improve physical characteristics. Processes for decellularizing harvested native tissue and repopulating it with new cells have been described (e.g., in U.S. Pat. No. 5,192,312 and U.S. Pat. No. 5,613,982). However, treatment of harvested tissues prior to decellularization has generally been limited to storage and/or preservation of the tissue.

According to the present invention, harvested native tissue from an animal or human donor is grown in culture. In certain embodiments of the invention the native tissue is seeded with cells before or after a culture period, although this is not a requirement. The cells may be of any of the types described above, but preferably the cells are derived from the same species as the intended recipient of the engineered tissue. In general, any of the culture methods and techniques described in the context of producing a tissue engineered construct may be employed in culturing harvested native tissue. For example, growth factors may be employed to promote cell growth or maintenance of a differentiated phenotype. Agents selected to promote adherence of cells may be applied to the native tissue. The harvested native tissue may be subjected to physical stimuli such as pulsatile stretch or fluid flow during the culture period as described above for tissue engineered constructs. Following one or more culture periods, during which one or more cell seedings may be performed, the native tissue is decellularized. The decellularized, engineered native tissue may be used for any of the purposes described above for decellularized tissue engineered constructs.

Thus in summary this inventive method includes the steps of (i) harvesting a native tissue; (ii) subjecting the native tissue to one or more tissue engineering steps to produce an engineered native tissue; and (iii) decellularizing the engineered native tissue to produce a decellularized, engineered native tissue. The tissue engineering step(s) comprise culturing the native tissue under conditions suitable for growth and can optionally include subjecting the native tissue to one or more cell seedings with optional intervening growth periods, subjecting the tissue to mechanical, electrical, and/or chemical stimuli. Such stimuli can include the application of pulsatile stretch or fluid flow forces, treating the native tissue with growth factors, etc. The decellularized, engineered native tissue can be used in any of the ways described above for a decellularized tissue engineered construct. Thus the decellularized, engineered native tissue can be implanted into the body of a subject or can be used for further tissue engineering. The decellularized, engineered native tissue can be stored and reconstituted as described above. The decellularized, engineered native tissue can be seeded with cells, e.g., cells derived from the intended recipient, and can be maintained in culture prior to implantation into the recipient. Mechanical, electrical, and/or chemical stimuli can be applied during the culture period(s) following decellularization.

EXAMPLES

Example 1

Preparation of a Primary Cell-Seeded Construct

This example describes the preparation of a tissue engineered construct suitable for decellularization, in this case a small caliber artery, using a bioreactor system. A more detailed description of many aspects of this process is found in the pending application referenced above. As an initial step, a non-woven mesh made of fine polyglycolic acid (PGA) fibers (Albany International Research Co., Mansfield, Mass.) was produced and further processed to yield a porous substrate with a hydrophilic surface. The processing enhances wettability and increases the number of cells which are deposited on the surface during seeding. Briefly, the treatment began with three successive 30 minute washes in hexane, dichloromethane, and diethyl ether followed by lyophilization overnight. The PGA mesh was then placed briefly in ethanol, removed to distilled water, and placed in a 1.0 normal solution of NaOH for 1 minute, during which the solution was agitated. The mesh was then washed successively in distilled water, changing the solution until the pH of the wash solution remained at approximately 7.0. The mesh was then lyophilized overnight. The mesh was rolled into tubes with inner diameters of approximately 3–6 mm and lengths of approximately 1–10 cm which were then sewn together with uncoated PGA suture (Davis & Geck, Inc., Manati, P.R.) to form a tubular substrate.

FIG. 1 depicts the bioreactor system (10), assembled appropriately for cell seeding. The bioreactor includes a glass chamber (22) with a volume of approximately 200 ml and hollow side-arms (12) with a 4 mm internal diameter. The side-arms are attached to tubular plastic connectors (24) within the vessel. A short tubular sleeve (26) of non-degradable Dacron vascular graft material (Sherwood-Davis & Geck, St. Louis, Mo.) having an approximately 5 mm internal diameter is sutured to the plastic connector on either side of the bioreactor. The Dacron sleeve, which is highly porous, functions as an anchor to attach the developing tissue to the plastic and glass of the bioreactor system. Smooth muscle cells and fibroblasts grow easily into the pores, thus allowing formation of a continuous connection between the cellular tissue and the non-degradable elements of the system.

In preparation for production of a vascular scaffold the ends of the tubular PGA substrate (16) were sutured to the Dacron sleeves using uncoated Dacron suture (Sherwood-Davis & Geck, St. Louis, Mo.). A length of highly distensible medical-grade silicone tubing (14) with a known compliance (Patter Products, Beaverton, Mich.) was inserted through the side-arms, plastic connectors, and Dacron sleeves. The bioreactor system, including the tubular substrate, was sterilized by exposure to ethylene oxide and allowed to outgas for at least 3 days.

Bovine aortic smooth muscle cells were obtained as follows. Explants of bovine thoracic aorta were obtained from a local abattoir on ice. Aortas were placed in PBS supplemented with penicillin at standard concentrations (100 U/ml). The intimal layer of the aortas was stripped away with forceps, and the outer adventitia was removed along with the outer media. The remaining middle portion of the media was laid down in a petri dish with the previously endothelial side down, and the tissue was scored at 1 cm intervals. Sufficient DMEM with Pen/Strep and 15% FBS was added to cover the bottom of the dish, without causing the tissues to float above the surface. The tissues were cultured for 7 to 10 days, during which smooth muscle cells migrated off the tissues to form a monolayer in the dish at the end of the culture period. The tissues were then removed, and the cells were cultured for a total of 2–3 passages. Smooth muscle identity and purity were confirmed by visual appearance and by immunostaining for smooth muscle α-actin. Cells were removed from culture by trypsinization (0.05% trypsin, 0.02% EDTA), centrifuged to a pellet, and gently resuspended to form a single cell suspension in fresh DMEM.

The substrate was seeded by evenly pipetting 1–2 ml of a suspension of bovine aortic smooth muscle cells at a concentration of approximately $5 \times 10^6$/ml onto the substrate. Cells were allowed to attach for approximately 30 minutes, and then fresh medium was added to the bioreactor vessel. The engineered vessel was cultured in the bioreactor for 8 weeks in an atmosphere of 10% $CO_2$ at a temperature of 37° C. in DMEM supplemented with 20% FBS, penicillin G (100 U/ml), 5 mM HEPES, ascorbic acid (0.05 mg/ml), $CuSO_4$ (3 ng/ml), proline (0.05 mg/ml), alanine (0.03 mg/ml), and glycine (0.05 mg/ml) with continuous stirring. Ascorbic acid was replenished daily. Approximately half the medium was replaced with fresh medium twice per week. Thus a volume of fresh medium equivalent to the volume of the bioreactor was supplied each week.

Example 2

Decellularization of a Tissue Engineered Bovine Artery Construct Using Ionic Detergent Solutions Materials and Methods Small caliber arteries were engineered using bovine aortic smooth muscle cells as described in Example 1. After an 8 week culture period a vessel was removed from the bioreactor, washed with PBS, and sliced into segments 2 mm thick. The slices were immersed in 50 ml of a decellularization solution containing 1 M NaCl, 25 mM EDTA, 8 mM CHAPS in sterile PBS at pH 7.2. The samples were incubated with continuous stirring for 1 hour at room temperature and were then washed three times in PBS. The samples were then placed in 50 ml of a second decellularization solution containing 1 M NaCl, 25 mM EDTA, 1.8 mM SDS in sterile PBS at pH 7.2 and incubated for 1 hour at room temperature with continuous stirring. After removal from the decellularization solution the segments were washed twice with PBS for 5 minutes to remove residual solution.

The decellularized artery and a control artery that had been produced under identical conditions but not subjected to decellularization were fixed in formalin, embedded in paraffin, sectioned, and stained with hematoxylin and eosin according to standard techniques.

Results

FIG. 2 shows low-power (66×, panel A) and high-power (100×, panel B) photomicrographs of untreated control vessels. In panel A, the outer surface of the vessel wall is at the right, and the inner (luminal) surface is to the left. As shown in the figure, the outermost portion of the vessel is composed almost entirely of cells (visible as small dark purple spots) and extracellular matrix. The innermost third of the vessel also contains circular polymer fragments, which are incorporated into the engineered vessel in a disorganized fashion. In the higher powered view of panel B, the outer surface of the vessel is oriented downward.

FIG. 3 shows low-power (66×, panel C) and high-power (100×, panel D) photomicrographs of the decellularized vessel. The inner surface of the vessel is oriented towards the right in panel C. As shown in the figure, polymer fragments are more loosely incorporated into the vessel architecture than in the control artery. Panel D shows the tissue portion of the vessel with the outer surface on the right. Some cellular fragments are visible, especially in the outermost portions of the vessel wall, but the overall number of cells and cellular remnants is significantly reduced compared with the control artery.

Example 3

Decellularization of a Tissue Engineered Bovine Artery Construct Using a Nonionic Detergent Solution Materials and Methods Small caliber arteries were engineered using bovine aortic smooth muscle cells as described in Example 1. After an 8 week culture period a vessel was removed from the bioreactor, rinsed with PBS, and sliced into segments 2 mm thick. The slices were immersed in 50 ml of a decellularization solution containing 1% Triton X-100® (Sigma), 0.02% EDTA (Sigma), 20 µg/ml RNAse A (Sigma), and 0.2 mg/ml DNAse (Sigma) in sterile PBS without $Ca^{2+}$ or $Mg^{2+}$ and incubated for 24 hours in a 10% $CO_2$ atmosphere at 37° C. with continuous stirring. After removal from the decellularization solution, the segments were washed several times with PBS to remove residual solution.

The decellularized artery and a control artery that had been produced under identical conditions but not subjected to decellularization were fixed in formalin, embedded in paraffin, sectioned, and stained with hematoxylin and eosin according to standard techniques.

Results

FIG. 4 shows low-power (66×, panel E) and high-power (100×, panel F) photomicrographs of the decellularized vessel. The outer surface of the vessel is oriented towards the right in panel E. As shown in the figure, polymer fragments (34) are very loosely adherent to the remaining collagen matrix. Panel F shows the tissue portion of the vessel, with very few remnants of nuclear material remaining between collagen strands. In comparison with the control artery shown in FIG. 2, the number of cells and cellular remnants is significantly reduced.

Example 4

Decellularization of a Tissue Engineered Porcine Artery Construct Using Ionic Detergent Solutions Materials and Methods Porcine carotid artery smooth muscle cells were obtained as follows. Explants of porcine carotid artery were obtained from a local abattoir on ice. Aortas were placed in PBS supplemented with penicillin at standard concentrations (100 U/ml). The intimal layer of the aortas was stripped away with forceps, and the outer adventitia was removed along with the outer media. The remaining middle portion of the media was laid down in a petri dish with the previously endothelial side down, and the tissue was scored at 1 cm intervals. Sufficient DMEM with Pen/Strep and 101% FBS was added to cover the bottom of the dish, without causing the tissues to float above the surface. The tissues were cultured for 7 to 10 days, during which smooth muscle cells migrated off the tissues to form a monolayer in the dish at the end of the culture period. The tissues were then removed, and the cells were cultured for a total of 2–3 passages. Smooth muscle identity and purity were confirmed by visual appearance and by immunostaining for smooth muscle α-actin. Cells were removed from culture by trypsinization (0.05% trypsin, 0.02% EDTA), centrifuged to a pellet, and gently resuspended to form a single cell suspension in fresh DMEM.

A small caliber artery was engineered using porcine carotid smooth muscle cells essentially as described in Example 1 except that the medium used was supplemented with 10% FBS rather than 20% FBS. After an 8 week culture period the vessel was removed from the bioreactor, washed with PBS, and sliced into segments 2 mm thick. The slices were immersed in 50 ml of a decellularization solution containing 1 M NaCl, 25 mM EDTA, 8 mM CHAPS in sterile PBS at pH 7.2. The samples were incubated with continuous stirring for 4 hours at room temperature and were then washed three times in PBS. The samples were then placed in 50 ml of a second decellularization solution containing 1 M NaCl, 25 mM EDTA, 1.8 mM SDS in sterile PBS at pH 7.2 and incubated for 4 hours at room temperature with continuous stirring. After removal from the decellularization solution the segments were washed twice with PBS for 5 minutes to remove residual solution.

The decellularized artery was fixed in formalin, embedded in paraffin, sectioned, and stained with hematoxylin and eosin according to standard techniques.

Results

Figure 5A:
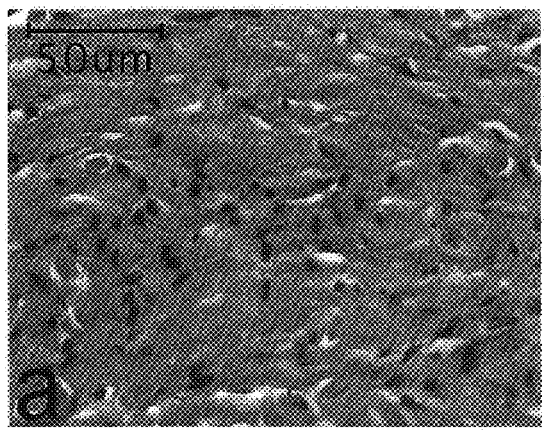
FIG. 5A shows a photomicrograph of a tissue engineered small caliber porcine artery prior to decellularization, stained with hematoxylin and eosin.
Figure 5B:
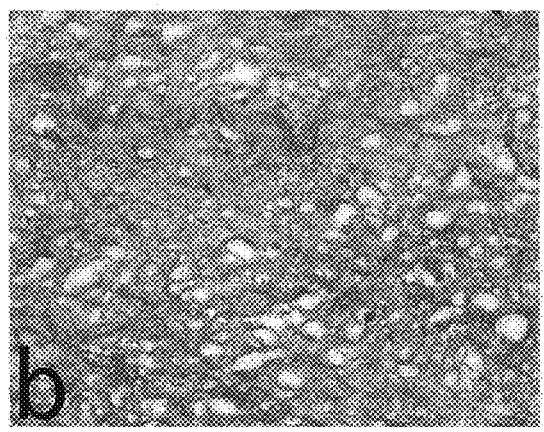
FIG. 5B shows a photomicrograph of a tissue engineered small caliber porcine artery following decellularization, stained with hematoxylin and eosin.

FIG. 5A shows a photomicrograph of a portion of the engineered vessel prior to decellularization. The image shows a donut-shaped cross-section of the vessel. The purple cell nuclei are clearly visible, and the extracellular matrix is stained pink. FIG. 5B shows a photomicrograph of a portion of the same vessel after decellularization. The almost complete absence of nuclear material suggests that the decellularization protocol effectively removed the great majority of cells while leaving the extracellular matrix substantially intact. It is likely that shorter periods of immersion in the decellularization solutions (e.g., 30 min to 4 hours) would also yield acceptable results.

Using this protocol there is no evidence of remaining polymeric substrate after decellularization. This finding suggests that the decellularization periods employed with the porcine vessel may more effectively remove the substrate than the shorter time periods employed to decellularize the bovine vessel described above.

Example 5

Decellularization and Reseeding of a Cultured Native Tissue Construct

Materials and Methods

Porcine carotid artery smooth muscle cells were obtained as describe in Example 4. To facilitate visualization after seeding, cells were fluorescently labeled with red fluorescent dye PKH26-GL (Sigma) according to the manufacturer's instructions.

A segment of native adult porcine carotid artery was decellularized in a two-phase treatment of solutions. The artery was harvested as follows, according to a protocol similar to that described in Swindle, M. M., Moody, D. C., Phillips, L. D., Swine as Models in Biomedical Research, Ames, Iowa, Iowa State University Press, 1992. Anesthesia was induced with Tiletamine 2.0 mg/kg+Zolazepam 8.8 mg/kg IM, supplemented with intermittent boluses of Xylazine 2.2 mg/kg 1M every 1–2 hours as needed. Anesthesia was maintained with Forane, 2%, during the length of the procedures. The left lateral neck was prepped and draped. The left common carotid artery was exposed, ligated, and excised for a length of 2–3 cm. The incision was closed in layers.

The harvested artery was placed in DMEM for transport (~10 min) and then immediately placed into decellularization solution. For the first twenty-four hours, the artery was submerged in PBS-based 8 mM CHAPS, 1M NaCl, and 25 mM EDTA. The solution was then changed to 1.8 mM SDS, 1M NaCl, and 25 mM EDTA for an additional 24 hours. Both treatments were conducted under sterile conditions at 37° C. and 10% $CO_2$ with stirring. After decellularization, the vessel was rinsed thoroughly in PBS.

A segment of vessel was suspended in a sterile bioreactor and seeded with fluorescently labeled porcine carotid artery smooth muscle cells by evenly pipetting 1–2 ml of cell suspension at a concentration of approximately $7 \times 10^6$/ml onto the outer surface of the decellularized vessel. The cells were allowed to attach for twenty minutes, and the seeded vessel was placed in a bioreactor as described above. The bioreactor was filled with 250 ml of DMEM culture medium supplemented with 10% FBS, penicillin G (100 U/ml), 5 mM HEPES, ascorbic acid (0.05 mg/ml), $CuSO_4$ (3 ng/ml), proline (0.05 mg/ml), alanine (0.03 mg/ml), and glycine (0.05 mg/ml). Ascorbic acid was replenished daily.

The vessel was cultured for three days in a 10% $CO_2$ atmosphere at a temperature of 37° C. with stirring. The vessel was then removed from the bioreactor, and segments were frozen for histology by first submerging in OCT (optimum cutting temperature) compound a widely available formulation of water soluble glycols and resins and then placing in liquid nitrogen. The segments were sliced in a frozen state and mounted on slides, which were kept frozen until examined under the microscope.

Results

FIG. 6 shows (A) a phase contrast view of a vessel cross section and (B) the corresponding fluorescent cross section. Since they were fluorescently labeled prior to seeding, seeded cells can be distinguished from residual cells remaining after the decellularization procedure. The presence of fluorescent cells on the vessel surface as seen in FIG. 6B indicated that seeded cells attached to the decellularized native vessel, but no inward migration occurred.

Example 6

Preparation of a Decellularized Tissue Engineered Bovine Construct Using a Nonionic Detergent Solution A small caliber artery is engineered using bovine aortic smooth muscle cells as described in Niklason, et al., Functional arteries grown in vitro, Science, 284: 489–93,1999. Briefly, 1–2 ml of a suspension of smooth muscle cells ($5 \times 10^6$ cells/ml) isolated from the medial layer of bovine aorta (as described in Ross, R., et al., J. Cell. Biol. 50, 172, 1999, the contents of which are incorporated herein by reference) are pipetted onto a tubular polyglycolic acid substrate that is secured in a bioreactor chamber over a length of distensible silicone tubing. The surface of the substrate is modified with sodium hydroxide as described in Gao, J., et al, *J. Biomed Mater. Res.* 42, 417, 1998, the contents of which are herein incorporated by reference, to increase surface hydrophilicity. After an initial seeding period of 30 min, the bioreactor is filled with medium (DMEM modified as described in Example 1). The construct is cultured for 8 weeks during which pulsatile radial stress is applied to the developing construct at 165 beats per minute and 5% radial distention (strain) by pumping medium through the distensible silicone tubing in a pulsatile fashion. Following the 8 week culture period the silicone tubing is removed, and the flow of medium is applied directly through the cultured vessel. To produce an endothelial layer, a suspension of bovine aortic endothelial cells ($3 \times 10^6$ cells/ml) is injected into the lumen, and the cells are allowed to adhere for 90 min. Luminal flow rate is gradually increased from 0.033 to 0.1 ml/sec over 3 days of culture, with corresponding shear stresses at the vessel wall of $1 \times 10^{-2}$ N/m$^2$ to $3 \times 10^{-2}$ N/m$^2$. The construct is cultured for an additional two weeks during which it is subjected to intraluminal flow.

Following the culture periods, the medium is drained from the bioreactor, and the construct is rinsed with sterile PBS. The bioreactor vessel is filled with a decellularization solution containing 1% Triton X-100® (Sigma), 0.02% EDTA (Sigma), 20 µg/ml RNAse A (Sigma), and 0.2 mg/ml DNAse (Sigma) in sterile PBS without Ca$^{2+}$ or Mg$^{2+}$. Decellularization solution is also placed in a flow system attached to the bioreactor and is pumped through the inner lumen of the vessel at a flow rate of approximately 0.1 ml/sec. After 24 hours of exposure to the decellularization solution at 37° C. in a 10% CO$_2$ atmosphere at 37° C. with continuous stirring, the decellularization solution is removed from the bioreactor and flow system, and the system is rinsed with PBS. The application of intraluminal flow through the interior of the engineered vessel results in removal of substantially all of the remaining fragments of the polymeric substrate.

For cryopreservation, the decellularized construct is first immersed for 20 min in HEPES-buffered DMEM containing 1 M DMSO, 2.5% chondroitin sulfate, and 10% fetal bovine serum at 4° C. and then cooled at a controlled rate of approximately 1.0°/min to –80° C. and transferred to liquid nitrogen for storage. Thawing is accomplished by immersing the storage container in a waterbath at 37° C. until all ice has disappeared, after which the container is transferred sequentially for 5 minute periods to DMEM containing 0.5 M, 0.25 M, and finally 0 M mannitol as an osmotic buffer. The decellularized vessel is implanted into the right saphenous artery of a Yucatan miniature pig as described in Niklason, et al., Functional arteries grown in vitro, *Science*, 284: 489–93,1999.

Example 7

Preparation and Subsequent Engineering of a Decellularized Tissue Engineered Construct A vascular tissue engineered construct is produced in a plastic bioreactor system similar to that described in Example 1, but without the use of a polymer substrate, as follows: Human smooth muscle cells and human endothelial cells are obtained using standard biopsy and culture techniques and are maintained in vitro. The length of silicone tubing extending between the Dacron sleeves in the bioreactor is coated in a sterile fashion with a thin layer of a gelatin material, e.g., made from dilute human collagen. Human collagen (commercially available) is denatured and pipetted or applied with a syringe onto the outside of the silicone tubing to create a layer approximately 50 µm thick. The tubing may be rotated during application of the collagen solution so that a layer of uniform thickness is produced. Thus according to this embodiment of the invention the collagen-coated tubing serves as the substrate.

After the collagen layer is allowed to dry, a suspension of 1 to 2 ml of culture medium containing human smooth muscle cells at a concentration of approximately 5 million cells/ml medium, is applied to the coated tubing and the Dacron sleeves on either end using a pipet. The tubing is preferably rotated during application of the cells to create an even distribution of cells. The thin coating allows an initial layer of cells to adhere to the outside of the tubing. The bioreactor stopper is replaced, and the cells are allowed to adhere for 30–60 minutes, after which the bioreactor and fluid reservoir are filled with culture medium (DMEM supplemented as described in Example 1). The bioreactor is placed in a tissue culture incubator and maintained at 37° C. in a 10% CO$_2$ atmosphere for a period of about 1 to 7 days during which pulsatile radial stress is applied to the developing construct at 165 beats per minute and 5% radial distention (strain) by pumping medium through the distensible silicone tubing in a pulsatile fashion.

Following this initial growth period, the stopper is removed, and the medium is drained from the bioreactor. The surface of the developing tissue on the tubing is then reseeded with a suspension of human smooth muscle cells substantially equivalent to those used in the initial seeding, and these cells are allowed to adhere to the developing tissue. The bioreactor is then filled with medium, and the culture process is repeated with physical stimuli applied as in the first growth period. This sequence (i.e., reseeding followed by a growth period) is continued until a tissue of desired thickness (e.g., approximately 0.038 cm) is produced on the tubing (approximately 8 weeks).

After the vessel has reached the desired thickness the silicone tubing is removed, and the flow of medium is applied directly through the cultured vessel. To produce an endothelial layer, a human endothelial cell suspension of $3 \times 10^6$ cells/ml in DMEM is injected into the lumen of the construct, and the cells are allowed to adhere for 90 min. Luminal flow rate is gradually increased from 0.033 to 0.1 ml/sec over 3 days of culture, with corresponding shear stresses at the vessel wall of $1 \times 10^{-2}$ N/m$^2$ to $3 \times 10^{-2}$ N/m$^2$. The construct is cultured for an additional two weeks during which it is subjected to intraluminal flow.

Following this second growth period, the medium is removed from the bioreactor chamber, and the construct is rinsed with PBS. The chamber is then filled with a decellularization solution containing 1 M NaCl, 25 mM EDTA, 1.8 mM SDS in sterile PBS at pH 7.2. Decellularization solution is also placed in a flow system attached to the bioreactor and is pumped through the inner lumen of the vessel at a flow rate of approximately 0.1 ml/sec in a pulsatile fashion. After 30 minutes of exposure to the decellularization solution at room temperature, the decellularization solution is removed from the bioreactor and flow system, and the system is rinsed with PBS.

For cryopreservation, the bioreactor chamber is first filled with HEPES-buffered DMEM containing 1 M DMSO, 2.5% chondroitin sulfate, and 10% fetal bovine serum at 4° C. Following a 20 minute period at 4° C., the chamber is cooled at a controlled rate of approximately 1.0° C./min to a temperature of −80° C. and transferred to liquid nitrogen for storage. After identification of a subject in need of a vascular graft, the decellularized vessel is thawed by immersing the bioreactor chamber in a waterbath at 37° C. until all ice has disappeared, after which the cryoprotection solution is drained from the chamber. For elution of the cryoprotection solution, the chamber is then filled sequentially for periods of 5 minutes with DMEM containing 0.5 M, 0.25 M, and finally 0 M mannitol as an osmotic buffer. The chamber is then filled with DMEM supplemented as described in Example 1.

Smooth muscle cells and endothelial cells are obtained from a biopsy specimen removed from the intended recipient of the construct. These cells are maintained in tissue culture and expanded. Following thawing of the decellularized construct, the outer surface of the construct is seeded with smooth muscle cells (1–2 ml of a suspension containing $5 \times 10^6$ cells/ml), which are allowed to adhere for 30 minutes. The bioreactor chamber is filled with culture medium, and the construct is maintained in culture for a period of 1 week. To produce an endothelial layer, a suspension of bovine aortic endothelial cells ($3 \times 10^6$ cells/ml) is injected into the lumen, and the cells are allowed to adhere for 90 min. The construct is cultured for an additional three days with the application of pulsatile stimuli as during the growth periods prior to decellularization and is then implanted into the recipient.

While the invention has been described and illustrated in connection with certain embodiments, many variations and modifications as will be evident to those skilled in this art may be made therein without departing from the spirit of the invention, and the invention as set forth in the claims is thus not to be limited to the precise details set forth above.

We claim:

1. A construct for use as a tissue engineering scaffold or for implanting into a subject comprising:

a tissue engineered construct comprising a 3-dimensional proteinaceous extracellular matrix that has been subjected to decellularization, wherein the tissue engineered construct was formed by seeding a substrate with cells and maintaining said cells under conditions suitable for growth of the cells, whereby a proteinaceous extracellular matrix surrounding said cells is formed, wherein the substrate comprises a collagen sponge.

2. A construct for use as a tissue engineering scaffold or for implanting into a subject comprising:

a tissue engineered construct comprising a 3-dimensional proteinaceous extracellular matrix that has been subjected to decellularization, wherein the tissue engineered construct was formed by seeding a substrate with cells and maintaining said cells under conditions suitable for growth of the cells, whereby a proteinaceous extracellular matrix surrounding said cells is formed, wherein the construct is treated so as to remove substantially all of the substrate.

3. A construct for use as a tissue engineering scaffold or for implanting into a subject comprising:

a tissue engineered construct comprising a 3-dimensional proteinaceous extracellular matrix that has been subjected to decellularization, wherein the tissue engineered construct was formed by seeding a substrate with cells and maintaining said cells under conditions suitable for growth of the cells, whereby a proteinaceous extracellular matrix surrounding said cells is formed, wherein the cells comprise porcine cells.

4. A construct for use as a tissue engineering scaffold or for implanting into a subject comprising:

a tissue engineered construct comprising a 3-dimensional proteinaceous extracellular matrix that has been subjected to decellularization, wherein the tissue engineered construct was formed by seeding a substrate with cells and maintaining said cells under conditions suitable for growth of the cells, whereby a proteinaceous extracellular matrix surrounding said cells is formed, wherein the cells comprise tumor cells.

* * * * *